(12) United States Patent
Oliphant et al.

(10) Patent No.: US 11,377,655 B2
(45) Date of Patent: Jul. 5, 2022

(54) SYNTHETIC NUCLEIC ACIDS HAVING NON-NATURAL STRUCTURES

(71) Applicant: Omniome, Inc., San Diego, CA (US)

(72) Inventors: Arnold Oliphant, San Diego, CA (US); James Yu, San Diego, CA (US)

(73) Assignee: PACIFIC BIOSCIENCES OF CALIFORNIA, INC., Menlo Park, CA (US)

(*) Notice: Subject to any disclaimer, the term of this patent is extended or adjusted under 35 U.S.C. 154(b) by 232 days.

(21) Appl. No.: 16/931,200

(22) Filed: Jul. 16, 2020

(65) Prior Publication Data

US 2021/0017517 A1    Jan. 21, 2021

Related U.S. Application Data

(60) Provisional application No. 62/874,601, filed on Jul. 16, 2019.

(51) Int. Cl.
| | | |
|---|---|---|
| *C12N 15/10* | (2006.01) | |
| *C40B 40/08* | (2006.01) | |
| *C12N 15/11* | (2006.01) | |

(52) U.S. Cl.
CPC ........ *C12N 15/1096* (2013.01); *C12N 15/111* (2013.01); *C40B 40/08* (2013.01)

(58) Field of Classification Search
CPC .............. C12N 15/1096; C12N 15/111; C12N 15/1093; C40B 40/08; C40B 40/06; C12Q 2525/155; C12Q 2525/191; C12Q 2525/197; C12Q 2535/122; C12Q 2563/149; C12Q 2563/179
See application file for complete search history.

(56) References Cited

U.S. PATENT DOCUMENTS

| | | |
|---|---|---|
| 4,469,863 A | 9/1984 | Ts'o et al. |
| 5,034,506 A | 7/1991 | Summerton et al. |
| 5,216,141 A | 5/1993 | Benner |
| 5,235,033 A | 8/1993 | Summerton et al. |
| 5,386,023 A | 1/1995 | Sanghvi et al. |
| 5,602,240 A | 2/1997 | De Mesmaeker et al. |
| 5,637,684 A | 6/1997 | Cook et al. |
| 5,641,658 A | 6/1997 | Adams et al. |
| 5,644,048 A | 7/1997 | Yau |

(Continued)

FOREIGN PATENT DOCUMENTS

| | | |
|---|---|---|
| WO | 9106678 A1 | 5/1991 |
| WO | 0063437 A9 | 6/2002 |

(Continued)

OTHER PUBLICATIONS

PCT/US2020/042380, "International Preliminary Report on Patentability", dated Jan. 27, 2022, 8 pages.

(Continued)

*Primary Examiner* — Jeremy C Flinders
*Assistant Examiner* — Taryn Kimberly Wood
(74) *Attorney, Agent, or Firm* — Kilpatrick Townsend & Stockton LLP

(57) ABSTRACT

Nucleic acid compositions having nucleotide sequences that do not occur in nature are provided. Also provided are populations of different nucleic acids having universal adapters or universal primer binding sites. Methods of capturing, copying or amplifying nucleic acids of interest using universal adapters, universal primer binding sites and/or universal primers are also provided.

23 Claims, 4 Drawing Sheets

Specification includes a Sequence Listing.

(56) References Cited

U.S. PATENT DOCUMENTS

| | | |
|---|---|---|
| 6,266,459 B1 | 7/2001 | Walt et al. |
| 6,355,431 B1 | 3/2002 | Chee et al. |
| 6,770,441 B2 | 8/2004 | Dickinson et al. |
| 6,859,570 B2 | 2/2005 | Walt et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,544,794 B1 | 6/2009 | Benner |
| 7,622,294 B2 | 11/2009 | Walt et al. |
| 8,034,923 B1 | 10/2011 | Benner et al. |
| 9,012,022 B2 | 4/2015 | George et al. |
| 10,710,076 B2 | 7/2020 | Oliphant et al. |
| 2002/0055100 A1 | 5/2002 | Kawashima et al. |
| 2004/0002090 A1 | 1/2004 | Mayer et al. |
| 2004/0096853 A1 | 5/2004 | Mayer |
| 2004/0125424 A1 | 7/2004 | Moon et al. |
| 2004/0132205 A1 | 7/2004 | Moon et al. |
| 2004/0233485 A1 | 11/2004 | Moon et al. |
| 2004/0263923 A1 | 12/2004 | Moon et al. |
| 2005/0064460 A1 | 3/2005 | Holliger et al. |
| 2005/0130173 A1 | 6/2005 | Leamon et al. |
| 2007/0099208 A1 | 5/2007 | Drmanac et al. |
| 2007/0128624 A1 | 6/2007 | Gormley et al. |
| 2008/0009420 A1 | 1/2008 | Schroth et al. |
| 2010/0111768 A1 | 5/2010 | Banerjee et al. |
| 2010/0120098 A1 | 5/2010 | Grunenwald et al. |
| 2011/0059865 A1 | 3/2011 | Smith et al. |
| 2012/0244525 A1 | 9/2012 | Hendrickson et al. |
| 2012/0270305 A1 | 10/2012 | Reed et al. |
| 2014/0249208 A1 | 9/2014 | Bancel et al. |
| 2015/0176071 A1 | 6/2015 | Fisher et al. |
| 2015/0368638 A1 | 12/2015 | Steemers et al. |
| 2016/0251650 A1 | 9/2016 | Steemers et al. |
| 2018/0016571 A1 | 1/2018 | Gloeckner et al. |
| 2018/0201925 A1 | 7/2018 | Steemers et al. |
| 2019/0048332 A1 | 2/2019 | Steemers et al. |
| 2019/0194692 A1 | 6/2019 | Meijrink et al. |
| 2020/0032317 A1 | 1/2020 | Rohrman et al. |

FOREIGN PATENT DOCUMENTS

| | | |
|---|---|---|
| WO | 2004018497 A2 | 3/2004 |
| WO | 2005010145 A2 | 2/2005 |
| WO | 2005065814 A1 | 7/2005 |
| WO | 2007123744 A2 | 11/2007 |

OTHER PUBLICATIONS

"Microsphere Selection Guide", Bangs Laboratories, Fishers Ind., 2018.
Ausubel et al., "Current Protocols in Molecular Biology", 1994-1998, John Wiley & Sons Publisher, vol. 1 & 2.
Beaucage et al., "The Functionalization of Oligonucleotides via Phosphoramidite Derivative", Tetrahedron, vol. 49, No. 10, Oct. 27, 1992, pp. 1925-1963.
Bentley et al., "Accurate Whole Human Genome Sequencing Using Reversible Terminator Chemistry", Nature, vol. 456, Nov. 6, 2008, pp. 53-59.
Brill et al., "Synthesis of Oligodeoxynucleoside Phosphorodithioates via Thiomid", Journal of American Chemist!}' Society, vol. 111, 1989, pp. 2321-2323.
Carlsson et al., "Screening for Genetic Mutations", Nature, vol. 380, 1996, p. 207.
De Mesmaeker et al., "Comparison of rigid and flexible backbones in antisense oligonucleotides", Bioorganic & Medicinal Chemistry Letters vol. 4, No. 3, 1994, pp. 395-398.
Dempcy et al., "Synthesis of a Thymidyl Pentamer of Deoxyribonucleic Guanidine and Binding Studies With DNA Homopolynucleotides.", Proceedings of the National Academy of Sciences, vol. 92, Jun. 1995, pp. 6097-6101.
Dressman et al., "Transforming Single DNA Molecules Into Fluorescent Magnetic Particles for Detection and Enumeration of Genetic Variations", Proceedings of the National Academy of Sciences of the United States of America, vol. 100, No. 15, Jul. 22, 2003, pp. 8817-8822.
Eckstein, "Oligonucleotides and Analogues: A Practical Approach", IRL Press, Oxford, 1991, 11 pages.
Egholm et al., "Peptide nucleic acids (PNA). Oligonucleotide analogs with an achiral peptide backbone", Journal of the American Chemical Society 114, 1995, pp. 1895-1897.
Egholm et al., "PNA hybridizes to complementary oligonucleotides obeying the Watson-Crick hydrogen-bonding rules", Nature 365, 1993, pp. 566-568.
Gao et al., "Unusual conformation of a 3'-thioformacetallinkage in DNA duplex", Journal of Biomolecular NMR, vol. 4, 1994, pp. 17-34.
Horn et al., "Oligonucleotides with alternating anionic and cationic phosphoramidate linkages: Synthesis and hybridization of stereo-uniform isomers", Tetrahedron Letters vol. 37, 1996, pp. 743-764.
Jenkins et al., "The Biosynthesis of Carbocyclic", Chemical Society Review, 1995, pp. 169-176.
Jung et al., "Hybridization of Alternating Cationic Anionic Oligonucleotides to RNA Segments", Nucleoside & Nucleotide, vol. 13, No. 6-7, 1994, pp. 1597-1605.
Kiedrowski et al., "Parabolic Growth of a Self-Replicating Hexadeoxynucleotide Bearing a 3'-5'-Phosphamidate Linkage", Angew. Chem. Int. Ed., vol. 30, 1991, pp. 423-426.
Letsinger et al., "Cationic oligonucleotides", Journal of American Chemistry Society, vol. 10, 1988, pp. 4470-4471.
Letsinger et al., "Effects of pendant groups at phosphorus on binding properties of d-ApA analogues", Nucleic Acids Research, vol. 14, 1986, pp. 3487-3499.
Letsinger et al., "Phosphoramidate Analogs of Oligonucleotides", Journal of Organic Chemistry, vol. 35, No. 11, 1970, pp. 3800-3803.
Lizardi et al., "Mutation Detection and Single-Molecule Counting Using Isothermal Rolling-Circle Amplification", Nature Genetics, vol. 19, No. 3, Jul. 1998, pp. 225-232.
Mag et al., "Synthesis and selective cleavage of an oligodeoxynucleotide containing a bridged internucleotide 5'-phosphorothioate linkage", Nucleic Acids Research, vol. 19, No. 7, 1991, pp. 1437-1441.
Meier et al., "Peptide Nucleic Acids (PNAs)-Unusual Properties of Nonionic Oligonucleotide Analogs", Angew. Chem. Int. Ed., vol. 31, No. 8, 1992, pp. 1008-1010.
Pauwels et al., "Biological Activity of New 2-5A Analogs", Chemica Scripta, vol. 26, 1986, pp. 141-145.
PCT/US2020/042380 , "Invitation to Pay Additional Fees and, Where Applicable, Protest Fee", Oct. 15, 2020, 2 pages.
Rawls, "Optimistic about antisense", Chemical & engineering news vol. 75, No. 22, 1997, pp. 35-39.
Sambrook et al., "Molecular Cloning: A Laboratory Manual", 3rd Edition, Cold Spring Harbor Laboratory Press, vol. 1, 2001, 79 pages.
Sawai et al., "Synthesis and Properties of Oligoadenylic Acids Containing 2'-5' Phosphoramide Linkage", Chemistry Letters, 1984, pp. 805-808.
Sprinzl et al., "Enzymatic Incorporation of ATP and CTP Analogues into the 3' End of tRNA", European Journal of Biochemistry, vol. 81,, 1977, pp. 579-589.
"Nitrosococcus Halophilus Nc4, Complete Genome", GenBank Accession No. CP001798.1, available online at: https://www.ncbi.nlm.nih.gov/nuccore/CP001798, Jan. 28, 2014, 15 pages.
PCT/US2020/042380, "International Search Report and Written Opinion", dated Dec. 22, 2020, 12 pages.

SYNTHETIC NUCLEIC ACIDS HAVING NON-NATURAL STRUCTURES

CROSS REFERENCE TO RELATED APPLICATION

This application is based on, and claims the benefit of, U.S. Provisional Application No. 62/874,601, filed Jul. 16, 2019, and which is incorporated herein by reference.

BACKGROUND

The present disclosure relates generally to synthesis and analysis of nucleic acids, and has applicability to nucleic acid sequencing.

The determination of nucleic acid sequence information is an important part of biological and medical research. The sequence information is helpful for identifying genes associated with diseases and phenotypes, identifying potential drug targets, and understanding mechanisms of disease development and progress. Sequence information is an important part of personalized medicine, where it can be used to optimize the diagnosis, treatment, or prevention of disease for an individual patient.

BRIEF SUMMARY

The present disclosure provides isolated nucleic acid molecules having the sequence or the complement of any one of SEQ ID NOs:1-12. The present disclosure further provides a population of different nucleic acid molecules. The population can include a plurality of nucleic acid molecules, each of the nucleic acid molecules including a universal sequence region and a variable sequence region, wherein the sequence of the variable sequence region differs between different nucleic acid molecules in the population, wherein the sequence of the universal sequence region is the same for the nucleic acid molecules in the population, and wherein the universal sequence region includes the sequence or the complement of any one of SEQ ID NOs:1-12. Also provided are compositions comprising the isolated nucleic acid molecules of the population of different nucleic acid molecules and methods of making and using the same.

Also provided is a method for preparing a nucleic acid library. The method can include steps of attaching universal adapters to nucleic acid fragments from a genome, thereby producing a library of nucleic acid molecules, wherein each of the nucleic acid molecules in the library includes: (i) a variable sequence region that differs between the nucleic acid molecules in the library, and (ii) a universal sequence region that is the same for the nucleic acid molecules in the library, wherein the universal sequence region comprises the sequence or the complement of any one of SEQ ID Nos:1-12.

DETAILED DESCRIPTION

Figure 1:
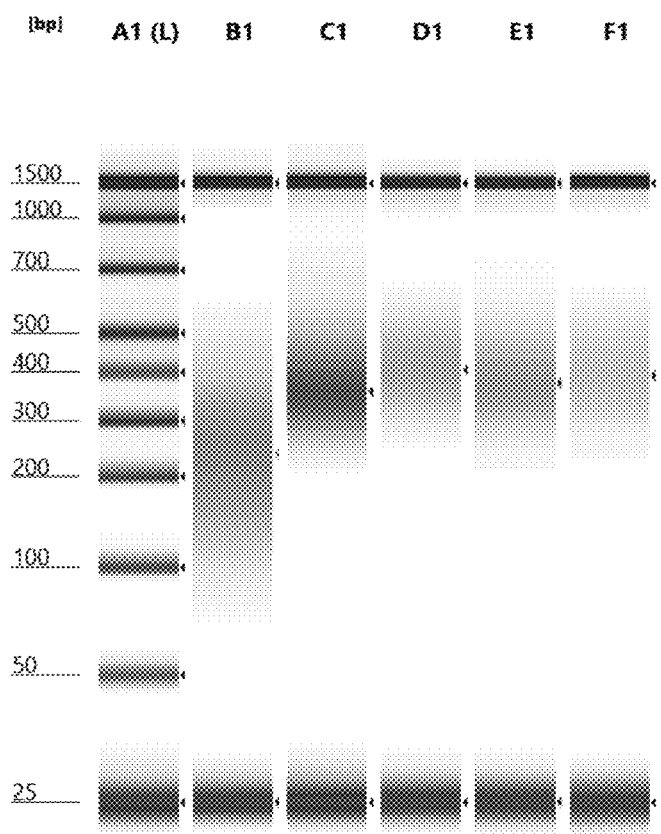
FIG. 1 is an image of a gel showing use of the provided isolated nucleic acid sequences as adapters and primers/primer binding sites. Lane A1 is ladder, lane B1 is sheared lambda DNA, lane C1 is version 1 an adapter of SEQ ID NOs:1, 3 and 4 as shown in FIG. 2, lane D1 is version 2 an adapter of SEQ ID NOs:1, 13 and 4, lane E1 is version 4 an adapter of SEQ ID NOs:1, 15 and 4 and lane F1 is version 3 an adapter of SEQ ID NOs:1, 14 and 4.

The present disclosure provides isolated nucleic acid molecules having nucleotide sequences that do not occur in nature. This uniqueness allows the sequences to provide a means for manipulating or characterizing entities (e.g. proteins, cells, larger nucleic acid molecules, synthetic molecules, and the like) to which they are attached, a capability that flows from the specificity with which complementary sequences bind to each other. For example, nucleic acid having a first sequence can be used as an analytical probe to detect a second nucleic acid having a sequence that complements the first sequence. Accordingly, the second nucleic acid can function as a tag for an entity to which it is attached or otherwise associated. Similarly, a nucleic acid having the first sequence can be used to manipulate a second nucleic acid having the complement of the first sequence. As such, the second nucleic acid can provide an affinity handle that is attached to an entity and the entity can be captured via complementary binding of the first sequence to the affinity handle. The compositions can be used for any of a variety of methods such as those that provide for synthesis, amplification or analysis of nucleic acids. Exemplary methods are set forth herein, known in the art or recognizable by those skilled in the art as useful when applied to the compositions set forth herein. Representative nucleic acid molecules of the present disclosure are set forth in Table 1.

TABLE 1

| NAME | SEQUENCE | SEQ ID NO |
|---|---|---|
| P1001F | 5'ACAGGTCGCCGTTGAG GCTACCAGCGGACAGA3' | 1 |
| C1001F | 5'TCTGTCCGCTGGTAGC CTCAACGGCGACCTGT3' | 2 |
| P1001R | 5'TGGTCTGCCGACTGGA CGAACGAGGGAGCGTA3' | 3 |
| C1001R | 5'TACGCTCCCTCGTTCG TCCAGTCGGCAGACCA3' | 4 |
| P1001F-A | 5'ACAGGTCGCCGTTGAG GCTACCAGCGGACAG3' | 5 |
| P1001R-A | 5'TGGTCTGCCGACTGGA CGAACGAGGGAGCGT3' | 6 |
| P1002F | 5'TAGAGCCCAGCACGACT CGCCGTATCAGCGGA3' | 7 |

TABLE 1-continued

| NAME | SEQUENCE | SEQ ID NO |
|---|---|---|
| C1002F | 5'TCCGCTGATACGGCGAGTCGTGCTGGGCTCTA3' | 8 |
| P1002R | 5'ACGCTTCGGTCGCTACGCACACCAACCCGTGA3' | 9 |
| C1002R | 5'TCACGGGTTGGTGTGCGTAGCGACCGAAGCGT3' | 10 |
| P1002F-A | 5'TAGAGCCCAGCACGACTCGCCGTATCAGCGG3' | 11 |
| P1002R-A | 5'ACGCTTCGGTCGCTACGCACACCAACCCGTG3' | 12 |

The sequences set forth in Table 1 are exemplified for nucleic acid molecules that have deoxyribonucleotides, wherein the deoxyribonucleotides have bases Adenine (A), Thymine (T), Guanine (G) or Cytosine (C). It will be understood, that one or more of the deoxyribonucleotides in any of the sequences can be replaced with ribonucleotides or other analogs, such as analogs set forth herein or known in the art. For example, the sequences can be ribonucleotide sequences in which the Thymine (T) bases are replaced with Uracil (U) bases. Generally, T and U bases can be used interchangeably for DNA or RNA molecules having the sequences of bases shown in Table 1.

The sequences set forth in Table 1 can be useful when used as primers for copying or amplifying nucleic acids when the nucleic acids comprise the complement of the sequence employed from Table 1. The sequences are designed to omit polyguanine sequences that are longer than two or three guanine bases, to preclude formation of secondary structures (e.g. hairpins), to omit sequences that are common in human genomes, to omit sequences that are common in a variety of genomes of particular interest for agricultural applications and research purposes, to position an adenine nucleotide at the 3' end and 5' end, and to have a 0.625 fraction of guanine and cytosine nucleotides. As used herein, the fraction of guanine and cytosine nucleotides refers to the fraction relative to the number of nucleotides over the length of the sequences of Table 1. Optionally, the fraction of guanine and cytosine nucleotides in the isolated nucleic acid molecules is at least 0.50, 0.60, 0.62, 0.625, 0.64, 0.66, 0.68, 0.70 or higher. Alternatively or additionally the range can be at most 0.70, 0.68, 0.66, 0.64, 0.625, 0.62, 0.60, 0.50 or lower. Optionally, the fraction is between 0.50 and 0.70, 0.50 and 0.60, or 0.60 and 0.70. Moreover, several of the sequences have the same melting temperature (Tm) as each other. Oligonucleotides having similar Tm can be advantageous for capturing or amplifying nucleic acids having sequence regions that are complementary to the oligonucleotides. Exemplary oligonucleotides that form useful pairs include, the pair of P1001F (SEQ ID NO:1) and P1001R (SEQ ID NO:3), the pair of C1001F (SEQ ID NO:2) and C1001R (SEQ ID NO:4), the pair of P1002F (SEQ ID NO:7) and P1002F (SEQ ID NO:9), and the pair of C1002F (SEQ ID NO:8) and C1002R (SEQ ID NO:10).

The nucleic acid sequences shown in Table 1 are complementary partners. For example, P1001F (SEQ ID NO:1) and C1001F (SEQ ID NO:2) are complementary partners; P1001R (SEQ ID NO:3) and C1001R (SEQ ID NO:4) are complementary partners; P1002F (SEQ ID NO:7) and C1002F (SEQ ID NO:8) are complementary partners; and P1002R (SEQ ID NO:9) and C1002R (SEQ ID NO:10) are complementary partners. By complementary partners, it is meant that the sequences are complements of each other. Stated another way, for example, P1001F (SEQ ID NO:1) is complementary to C1001F (SEQ ID NO:2) and C100F (SEQ ID NO:2) is complementary to P1001F (SEQ ID NO:1). The complementary partners can be useful as primers and primer binding sites, for example, serving as universal primers and universal priming sites for multiplex amplification or copying of nucleic acids that contain the priming sites. The complementary partners can also be used as probes and targets, for example, serving as universal probes and universal targets for multiplex capture of nucleic acids that contain the targets.

Optionally, it may be useful for the 3' end of a primer to end one nucleotide short of the 5' end of the primer binding site to which it will anneal. In this configuration the identity of the first nucleotide that will be added to the primer (e.g. via primer extension) will be known based on the identity of the 5' base in the primer binding site. Knowing the first nucleotide that will be added to a primer can be useful when the primer is used to determine the sequence of an unknown template, for example, when the primer is used as a universal primer for a population of different templates that have a universal primer binding site. In this case, the first nucleotide that is added to the primer can be detected as a quality control for subsequent sequencing or as a means to locate nucleic acids in a random array of nucleic acids. Exemplary sequences that can be used as primers that anneal to a longer primer binding site include P1001F-A (SEQ ID NO:5) which is a complementary partner to C1001F (SEQ ID NO:2); P1001R-A (SEQ ID NO:6) which is a complementary partner to C1001R (SEQ ID NO:4); P1002F-A (SEQ ID NO:11) which is a complementary partner to C1002F (SEQ ID NO:8); and P1002R-A (SEQ ID NO:12) which is a complementary partner to C1002R (SEQ ID NO:10).

The sequence of P1001F-A (SEQ ID NO:5) is identical to the sequence of P1001F (SEQ ID NO:1) without the 3' A base of the latter. The sequence of P1001R-A (SEQ ID NO:6) is identical to the sequence of P1001R (SEQ ID NO:3) without the 3' A base of the latter. The sequence of P1002F-A (SEQ ID NO:11) is identical to the sequence of P1002F (SEQ ID NO:7) without the 3' A base of the latter. The sequence of P1002R-A (SEQ ID NO:12) is identical to the sequence of P1002R (SEQ ID NO:9) without the 3' A base of the latter.

Definitions

Terms used herein will be understood to take on their ordinary meaning in the relevant art unless specified otherwise. Several terms used herein and their meanings are set forth below.

As used herein, the term "array" refers to a population of molecules attached to one or more solid support such that the molecules at one site can be distinguished from molecules at other sites. An array can include different molecules that are each located at different addressable sites on a solid support. Alternatively, an array can include separate solid supports each functioning as a site that bears a different molecule, wherein the different molecules can be identified according to the locations of the solid supports on a surface to which the solid supports are attached, or according to the locations of the solid supports in a liquid such as a fluid stream. The molecules of the array can be, for example, nucleotides, nucleic acids, nucleic acid primers, nucleic acid templates, primed template nucleic acids, or nucleic acid enzymes such as polymerases, ligases, exonucleases or combinations thereof.

As used herein, the term "attached" refers to the state of two things being joined, fastened, adhered, connected or bound to each other. For example, a nucleic acid can be attached to a solid phase support by a covalent or non-covalent bond. Similarly, two nucleic acids can be attached to each other by a covalent (e.g. phosphodiester) bond or by a non-covalent bond (e.g. hydrogen bonding between bases of the two nucleic acids). A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "blocking moiety," when used in reference to a nucleotide, means a part of the nucleotide that inhibits or prevents the 3' oxygen of the nucleotide from forming a covalent linkage to a next correct nucleotide during a nucleic acid polymerization reaction. The blocking moiety of a "reversibly terminated" nucleotide can be removed from the nucleotide analog, or otherwise modified, to allow the 3'-oxygen of the nucleotide to covalently link to a next correct nucleotide. Such a blocking moiety is referred to herein as a "reversible terminator moiety." Exemplary reversible terminator moieties are set forth in U.S. Pat. No. 7,427,673; 7,414,116; 7,057,026; 7,544,794 or 8,034,923; or PCT publications WO 91/06678 or WO 07/123744, each of which is incorporated herein by reference. A nucleotide that has a blocking moiety or reversible terminator moiety can be at the 3' end of a nucleic acid, such as a primer, or can be a monomer that is not covalently attached to a nucleic acid.

As used herein, the term "complexity," when used in reference to one or more nucleotide sequences, means the number of unique N-grams in the plurality. An "N-gram" is a contiguous sequence of n nucleotides in a given nucleotide sequence. The larger the number of unique N-grams in a plurality of nucleotide sequences, the higher the complexity of the plurality of nucleotide sequences. The complexity of a population of nucleic acid fragments can be compared to the complexity of a reference sequence by comparing the number of N-grams of a particular size in the population to the number of N-grams of that particular size in the reference sequence. The reference sequence can be from the same organism as the population of nucleic acids. However, the reference sequence and population of nucleic acids need not be from the same genome in order to compare their sequence complexities. When evaluating a population of nucleic acid fragments, the N-gram can be equivalent to the average length of the sequences in the population or equivalent to the average length of variable sequence regions in a population of nucleic acid fragments that contain one or more universal sequence. The N-gram length used to compare the complexity of a population of nucleic acid fragments to a reference genome can be at least 25 nucleotides, 50 nucleotides, 100 nucleotides, 250 nucleotides, 500 nucleotides, $1 \times 10^3$ nucleotides or more. Alternatively or additionally, the length of the N-gram can be capped to be no more than $1 \times 10^3$ nucleotides, 500 nucleotides, 250 nucleotides, 100 nucleotides, 50 nucleotides, 25 nucleotides or fewer. The reference genome can be a human genome or genome from another organism such as those set forth herein.

The term "comprising" is intended herein to be open-ended, including not only the recited elements, but further encompassing any additional elements.

As used herein, the term "deblock" means to remove or modify a reversible terminator moiety of a nucleotide to render the nucleotide extendable. For example, the nucleotide can be present at the 3' end of a primer such that deblocking renders the primer extendable. Exemplary deblocking reagents and methods are set forth in U.S. Pat. Nos. 7,427,673; 7,414,116; 7,057,026; 7,544,794 or 8,034,923; or PCT publications WO 91/06678 or WO 07/123744, each of which is incorporated herein by reference.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "exogenous," when used in reference to a moiety of a molecule, means a chemical moiety that is not present in a natural analog of the molecule. For example, an exogenous label of a nucleotide is a label that is not present on a naturally occurring nucleotide. Similarly, an exogenous linker that is present on a nucleic acid is not found on the nucleic acid in its native milieu.

As used herein, the term "extension," when used in reference to a nucleic acid, means a process of adding at least one nucleotide to the 3' end of the nucleic acid. The term "polymerase extension," when used in reference to a nucleic acid, refers to a polymerase catalyzed process of adding at least one nucleotide to the 3' end of the nucleic acid. A nucleotide or oligonucleotide that is added to a nucleic acid by extension is said to be incorporated into the nucleic acid. Accordingly, the term "incorporating" can be used to refer to the process of joining a nucleotide or oligonucleotide to the 3' end of a nucleic acid by formation of a phosphodiester bond.

As used herein, the term "extendable," when used in reference to a nucleotide, means that the nucleotide has an oxygen or hydroxyl moiety at the 3' position, and is capable of forming a covalent linkage to a next correct nucleotide if and when incorporated into a nucleic acid. An extendable nucleotide can be at the 3' position of a primer or it can be a monomeric nucleotide. A nucleotide that is extendable will lack blocking moieties such as reversible terminator moieties.

As used herein, a "flow cell" is a reaction chamber that includes one or more channels that direct fluid to a detection zone. The detection zone can be coupled to a detector such that a reaction occurring in the reaction chamber can be observed. For example, a flow cell can contain primed template nucleic acid molecules tethered to a solid phase support, to which nucleotides and ancillary reagents are iteratively applied and washed away. The flow cell can include a transparent material that permits the sample to be imaged after a desired reaction occurs. For example, a flow cell can include a glass or plastic slide containing small fluidic channels through which polymerases, dNTPs and buffers can be pumped. The glass or plastic inside the channels can be decorated with one or more primed template nucleic acid molecules to be sequenced. An external imaging system can be positioned to detect the molecules at a detection zone. Exemplary flow cells, methods for their manufacture and methods for their use are described in US Pat. App. Publ. Nos. 2010/0111768 A1 or 2012-0270305 A1; or WO 05/065814, each of which is incorporated by reference herein.

As used herein, the term "gel" is intended to mean a semi-rigid material that is permeable to liquids and gases. Typically, gel can swell when liquid is taken up and can contract when liquid is removed by drying. Exemplary gels include, but are not limited to, those having a colloidal structure, such as agarose; polymer mesh structure, such as gelatin; or cross-linked polymer structure, such as polyacrylamide. Useful gels are described, for example, in U.S. Pub. No. 2011/0059865, and U.S. Pat. No. 9,012,022, each of which is incorporated herein by reference. A gel can be attached to a nucleic acid, for example, as a means to mediate attachment of the nucleic acid to a solid phase support that is coated by the gel.

As used herein, the term "isolated," when used in reference to a nucleic acid molecule, refers to the nucleic acid molecule being separated to some degree from endogenous materials with which the nucleic acid molecule may naturally occur or exist. For example, the term can refer to a nucleic acid molecule that is separated from chromatin or other protein or components of genomic DNA. An isolated nucleic acid molecule can be a fragment that is shorter than a naturally occurring nucleic acid molecule from which it was derived or an isolated nucleic acid molecule can be a fragment that is shorter than an endogenous nucleic acid molecule having the same or complementary sequence. An isolated nucleic acid need not have been removed from a biological source, for example, having been produced by a synthetic technique.

As used herein, the term "label" refers to a molecule, or moiety thereof, that provides a detectable characteristic. The detectable characteristic can be, for example, an optical signal such as absorbance of radiation, fluorescence emission, luminescence emission, fluorescence lifetime, fluorescence polarization, or the like; Rayleigh and/or Mie scattering; binding affinity for a ligand or receptor; magnetic properties; electrical properties; charge; mass; radioactivity or the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, or the like.

As used herein, "linker" and "linker moiety" refer to an atom or molecular construct that joins two different entities. Typically, a linker will provide a covalent bond, or a series of covalent bonds, between the two entities. However, a linker can include non-covalent bonds such as those that form between a receptor and ligand. Exemplary entities that can be linked include, but are not limited to, a solid support, moiety (e.g. a nucleotide monomer of a nucleic acid or a base of a nucleotide) or molecule (e.g. a nucleic acid or label).

As used herein, the term "nucleotide" can be used to refer to a native nucleotide or analog thereof. Examples include, but are not limited to, nucleotide triphosphates (NTPs) such as ribonucleotide triphosphates (rNTPs), deoxyribonucleotide triphosphates (dNTPs), or non-natural analogs thereof such as dideoxyribonucleotide triphosphates (ddNTPs) or reversibly terminated nucleotide triphosphates (rtNTPs).

As used herein, the term "primer" refers to a nucleic acid having a sequence that binds to a nucleic acid at or near a template sequence. Generally, the primer binds in a configuration that allows replication of the template, for example, via polymerase extension of the primer. The primer can be a first portion of a nucleic acid molecule that binds to a second portion of the nucleic acid molecule, the first portion being a primer sequence and the second portion being a primer binding sequence (e.g. a hairpin primer). Alternatively, the primer can be a first nucleic acid molecule that binds to a second nucleic acid molecule having the template sequence. A primer can consist of DNA, RNA or analogs thereof. A primer can have an extendible 3' end or a 3' end that is blocked from primer extension.

As used herein, the term "site," when used in reference to an array, means a location in an array where a particular molecule is present. A site can contain only a single molecule or it can contain a population of several molecules of the same species (i.e. an ensemble of the molecules). Alternatively, a site can include a population of molecules that are different species (e.g. a population of different template sequences). Sites of an array are typically discrete. The discrete sites can be contiguous or they can have spaces between each other. An array useful herein can have, for example, sites that are separated by less than 100 microns, 50 microns, 10 microns, 5 microns, 1 micron, or 0.5 micron. Alternatively or additionally, an array can have sites that are separated by greater than 0.5 micron, 1 micron, 5 microns, 10 microns, 50 microns or 100 microns. The sites can each have an area of less than 1 square millimeter, 500 square microns, 100 square microns, 25 square microns, 1 square micron or less. The density of sites of sites in an array can be, for example, at least about 10 sites/cm$^2$, 100 sites/cm$^2$, $1 \times 10^3$ sites/cm$^2$, $1 \times 10^4$ sites/cm$^2$, $1 \times 10^5$ sites/cm$^2$, $1 \times 10^6$ sites/cm$^2$, or higher.

As used herein, the term "solid support" or "solid phase support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, the term "type" is used to identify molecules that share the same chemical structure. For example, a mixture of nucleotides can include several dCTP molecules. The dCTP molecules will be understood to be the same type of nucleotide as each other, but a different type of nucleotide compared to dATP, dGTP, dTTP etc. Similarly, individual DNA molecules that have the same sequence of nucleotides are the same type, whereas DNA molecules with different sequences are different types. The term "type" can also identify moieties that share the same chemical structure. For example, the cytosine bases in a template nucleic acid will be understood to be the same type of base as each other independent of their position in the template sequence.

As used herein, the term "universal sequence" means a sequence of nucleotides that is the same for two or more nucleic acid molecules. The sequence that is universal to two or more nucleic acids can include all or part of the nucleic acids that are being compared. The universal sequence can have a length of at least 10, 25, 50, 100, or more nucleotides. Alternatively or additionally, the length can be at most 100, 50, 25, 10, or fewer nucleotides.

As used herein, the term "variable sequence," when used in reference to a plurality of nucleic acid molecules, means regions of sequence that are different between the nucleic acid molecules in the plurality. The regions that are variable between two or more nucleic acids can include all or part of the nucleic acids that are being compared. The variable sequence region can have a length of at least 100, 250, 500, $1\times10^3$, $1\times10^4$, $1\times10^6$, or more nucleotides. Alternatively or additionally, the length can be at most $1\times10^6$, $1\times10^4$, $1\times10^3$, 500, 100, 250, or fewer nucleotides. The disclosure set forth below and recited in the claims can be understood in view of the above definitions.

Exemplary Nucleic Acids

The present disclosure provides an isolated nucleic acid molecule comprising or consisting of the sequence or the complement of any one of SEQ ID NOs:1-12. The isolated nucleic acid molecule can be single stranded or double stranded. A double stranded nucleic acid molecule can include the sequence of any one of SEQ ID NOs:1-12 in a first strand and the second strand can include the complement of any one of SEQ ID NOs:1-12 that is present in the first strand. Optionally, a nucleic acid strand can include the sequence of any one of SEQ ID NOs:1-12 and the complement of any one of SEQ ID NOs:1-12 that is present in the strand. For example, the nucleic acid strand can be in a hairpin structure or can be capable of forming a hairpin structure.

Optionally, the number of nucleotides in a nucleic acid strand will be the same as the number of nucleotides in the sequence or the complement of any one of SEQ ID NOs: 1-12. Alternatively, the isolated nucleic acid molecule can have one or more strands that are longer than the sequence or the complement of any one of SEQ ID NOs:1-12. For example, a nucleic acid strand can include a first region that includes the sequence or the complement of any one of SEQ ID NOs:1-12 and the strand can further include a second region having one or more additional nucleotides. The regions can be contiguous in the strand. However, the regions need not be contiguous and can instead be separated by a linker. The linker can be composed of nucleotides and/or non-nucleotide moieties. Whether or not the regions are contiguous, a region of a nucleic acid strand that includes the sequence or the complement of any one of SEQ ID NOs:1-12 can be located on the 5' side of the second region, or on the 3' side of the second region. Optionally, a region of a nucleic acid strand that includes the sequence or the complement of any one of SEQ ID NOs:1-12 can be flanked on both sides by other regions that contain one or more nucleotides.

Optionally, the 3' end of the sequence or the complement of any one of SEQ ID NOs:1-12 can be present at the 3' end of a nucleic acid strand. Alternatively or additionally, the 5' end of the sequence or the complement of any one of SEQ ID NOs:1-12 can be present at the 5' end of a nucleic acid strand.

Thus, provided is an isolated nucleic acid molecule comprising the sequence or the complement of SEQ ID NO:1, SEQ ID NO:2, SEQ ID NO:7 or SEQ ID NO:8. Optionally, the 3' end of the sequence of SEQ ID NO:1, SEQ ID NO:2, SEQ ID NO:7 or SEQ ID NO:8 is the 3' end of a strand of the isolated nucleic acid molecule, or wherein the 3' end of the complement of SEQ ID NO:1, SEQ ID NO:2, SEQ ID NO:7 or SEQ ID NO:8 is the 3' end of a strand of the isolated nucleic acid molecule. Optionally, the isolated nucleic acid molecule is single stranded. Optionally, the isolated nucleic acid molecule is double stranded, thereby having a first strand and a second strand. Optionally, the first strand of the isolated nucleic acid molecule comprises the sequence of SEQ ID NO:1, SEQ ID NO:2, SEQ ID NO:7, or SEQ ID NO:8 and wherein the second strand of the isolated nucleic acid comprises the complement of SEQ ID NO:1, SEQ ID NO:1, SEQ ID NO:2, SEQ ID NO:7, or SEQ ID NO:8. When the nucleic acid is RNA, then thymine is replaced by uracil in the sequences. Thus, when the nucleic acid comprises RNA, wherein thymine is replaced by uracil in SEQ ID NO:1, SEQ ID NO:2, SEQ ID NO:7, or SEQ ID NO:8 or the complement of SEQ ID NO:1, SEQ ID NO:2, SEQ ID NO:7, or SEQ ID NO:8. Optionally, the nucleic acid comprises a linker moiety, the linker moiety being exogenous to the nucleic acid. The linker moiety can be attached the nucleic acid to a label moiety, the label moiety being exogenous to the nucleic acid. The exogenous linker moiety can be attached the nucleic acid to a solid phase support. Optionally, the solid phase support comprises a bead. Optionally, the solid phase support comprises a site of a nucleic acid array. Optionally, the nucleic acid molecule is in solution phase.

The isolated nucleic acid molecule can further include the sequence or the complement of SEQ ID NO:3, SEQ ID NO:4, SEQ ID NO:9 or SEQ ID NO:10. Optionally, the 3' end of the sequence of SEQ ID NO:3, SEQ ID NO:4, SEQ ID NO:9, or SEQ ID NO:10 is the 3' end of a strand of the isolated nucleic acid molecule, or wherein the 3' end of the complement of SEQ ID NO:3, SEQ ID NO:4, SEQ ID NO:9, or SEQ ID NO:10 is the 3' end of a strand of the isolated nucleic acid molecule. The isolated nucleic acid molecule can be double stranded, thereby having a first strand and a second strand. Optionally, the first strand of the isolated nucleic acid molecule comprises the sequence of SEQ ID NO:3, SEQ ID NO:4, SEQ ID NO:9, or SEQ ID NO:10 and wherein the second strand of the isolated nucleic acid comprises the complement of SEQ ID NO:3, SEQ ID NO:4, SEQ ID NO:9, or SEQ ID NO:10. Optionally, the first strand of each of the nucleic acid molecules comprises the sequence of SEQ ID NO:1, SEQ ID NO:2, SEQ ID NO:7, or SEQ ID NO:8 and wherein the second strand of each of the nucleic acid molecules comprises the complement of SEQ ID NO:1, SEQ ID NO:2, SEQ ID NO:7, or SEQ ID NO:8. Optionally, the first strand of each of the nucleic acid molecules comprises the complement of SEQ ID NO:1, SEQ ID NO:2, SEQ ID NO:7, or SEQ ID NO:8 and wherein the second strand of each of the nucleic acid molecules comprises the sequence of SEQ ID NO:1, SEQ ID NO:2, SEQ ID NO:7, or SEQ ID NO:8. The isolated nucleic acid molecules can include (i) SEQ ID NO:1 and SEQ NO:3 or the complements thereof, (ii) SEQ ID NO:2 and SEQ ID NO:4, or the complements thereof, (iii) SEQ ID NO:7 and SEQ ID NO:9 or the complements thereof, or (iv) SEQ ID NO:8 and SEQ ID NO:10 or the complements thereof.

Also provided herein are isolated nucleic acids having at least 84%, 90%, 93%, 96%, identity to SEQ ID NOs:1-12. The term percent identity, in the context of two or more nucleic acids or polypeptide sequences, refer to two or more sequences or subsequences that are the same or have a specified percentage of amino acid residues or nucleotides that are the same (i.e., about 84%, 90%, 93%, 96%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site at ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. Employed algorithms can account for gaps and the like.

Thus, provided are nucleic acid sequences with one or more nucleotide substitutions. Optionally, SEQ ID NOs:1-12 include at most 4, 3, 2 or 1 nucleotide substitutions. For example, one or more nucleotides of SEQ ID NOs:1-12 can include one or more substitutions comprising a C for an A or T; a G for an A or T; an A for a G or C, a T for a G or C, or Inosine (I) for any one of A, T, C, or G. For example, SEQ ID NOs:1-12 can include 1, 2, 3 or 4 substitutions of A, T, C or G with I. Exemplary nucleic acid sequences having SEQ ID NO:3 with one or more nucleotide changes include, but are not limited to SEQ ID NO:13 (TGGTCTTC TGACTTGACGAACGAGTGAGCGTA), SEQ ID NO:14 (TGGTCTGIIGAITGGACGAAIGAGGGAGCGTA), and SEQ ID NO:15 (TGGTCTGICGACTGGACGAA IGAGGGAGCGTA). An advantage of SEQ ID NO:13, SEQ ID NO:14 and SEQ ID NO:15 over SEQ ID NO:3 is that the substitutions shift the propensity of the sequences from forming an intramolecular hybrid structure to having a higher relative propensity of forming an intermolecular hybrid with a second nucleic acid molecule such as SEQ ID NO:4. A structure referred to as a hairpin, hairpin loop or stem loop occur when two regions of the same strand, usually complementary in nucleotide sequence when read in opposite directions, base-pair to form a double helix that ends in a loop. In the example of SEQ ID NO:13, SEQ ID NO:14 and SEQ ID NO:15, the substitutions are positioned within one or both of the regions that could otherwise form such intramolecular structures. The introduced mismatches have a more significant adverse energetic impact on formation of the relatively short intramolecular hybrid region as compared to the intermolecular hybrid (e.g. hybrid between SEQ ID NO:3 and SEQ ID NO:4) which is longer. The nucleotide substitutions can be located in any position within SEQ ID NOs:1-12. Optionally, the substitutions are located at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32, from the 3' end of SEQ ID NOs:1-12. Alternatively or additionally, the substitutions are located at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32, from the 5' end of SEQ ID NOs:1-12.

Optionally, the substitutions are located in one or both complementary partners. For example, P1001F (SEQ ID NO:1) and C1001F (SEQ ID NO:2) are complementary partners; P1001R (SEQ ID NO:3) and C1001R (SEQ ID NO:4) are complementary partners; P1002F (SEQ ID NO:7) and C1002F (SEQ ID NO:8) are complementary partners; and P1002R (SEQ ID NO:9) and C1002R (SEQ ID NO:10) are complementary partners. The sequence of P1001F-A (SEQ ID NO:5) is identical to the sequence of P1001F (SEQ ID NO:1) without the 3' A base of the latter and is complementary to C1001F (SEQ ID NO:2). The sequence of P1001R-A (SEQ ID NO:6) is identical to the sequence of P1001R (SEQ ID NO:3) without the 3' A base of the latter and is complementary to C1001R (SEQ ID NO:4). The sequence of P1002F-A (SEQ ID NO:11) is identical to the sequence of P1002F (SEQ ID NO:7) without the 3' A base of the latter and is complementary to C1002F (SEQ ID NO:8). The sequence of P1002R-A (SEQ ID NO:12) is identical to the sequence of P1002R (SEQ ID NO:9) without the 3' A base of the latter and is complementary to C1002R (SEQ ID NO:10).

Complementary partners can be fully complementary at all positions relative to each other or they can include a mismatch at 1 or more positions relative to each other. Thus, SEQ ID NOs:1, 3, 5, 6, 7, 9, 11 or 12 can include one or more substitutions, for example, 1, 2, 3, or 4 substitutions while SEQ ID NOs:2, 4, 8, and 10 contain no substitutions. Alternatively, SEQ ID NOs:2, 4, 8 or 10 can include one or more substitutions, for example, 1, 2, 3, or 4 substitutions while SEQ ID NOs:1, 3, 5, 6, 7, 9, 11 or 12 contain no substitutions. Optionally, SEQ ID NOs:1, 3, 5, 6, 7, 9, 11 or 12 can include one or more substitutions, for example, 1, 2, 3, or 4 substitutions and SEQ ID NOs:2, 4, 8, and 10 can include one or more substitutions, for example, 1, 2, 3, or 4 substitutions. Optionally, the mismatches can be placed to reduce the relative propensity for forming intramolecular hybrid structures compared to intermolecular hybrid structures.

Thus, when a nucleic acid comprises both complementary partners the nucleic acid is double stranded. Thus, the nucleotide substitutions can be located on one or both strands depending on which complementary partner contains the substitutions. Thus, provided are nucleic acids having a double stranded region, the region comprising a first strand having SEQ ID NOs:1-12 or a variant thereof having one or more nucleotide substitutions and a second strand comprising the complement of SEQ ID NOs:1-12 or a variant thereof having one or more nucleotide substitutions. Optionally, the variant comprises at most 4, 3, 2 or 1 substitutions. For example, nucleic acids having a double stranded region can include a first strand comprising a variant of P1001F (SEQ ID NO:1) or P1001F-A (SEQ ID NO:5), wherein the variant comprises one or more substitutions and a second strand comprising C1001F (SEQ ID NO:2). Nucleic acids having a double stranded region can include a first strand comprising a variant of P1001R (SEQ ID NO:3) or P1001R-A (SEQ ID NO:6), wherein the variant comprises one or more substitutions and a second strand comprising C1001R (SEQ ID NO:4). Nucleic acids having a double stranded region can include a first strand comprising a variant of P1002F (SEQ ID NO:7) or P1002F-A (SEQ ID NO:11), wherein the variant comprises one or more substitutions and a second strand comprising C1002F (SEQ ID NO:8). Nucleic acids having a double stranded region can include a first strand comprising a variant of P1002R (SEQ ID NO:9) or P1002R-A (SEQ ID NO:12), wherein the variant comprises one or more substitutions and a second strand comprising C1002R (SEQ ID NO:10). Optionally, the variant comprises at most 4, 3, 2 or 1 substitutions.

Optionally, nucleic acids having a double stranded region can include a first strand comprising P1001F (SEQ ID NO:1) or P1001F-A (SEQ ID NO:5) and a second strand comprising a variant of C1001F (SEQ ID NO:2), wherein the variant comprises one or more substitutions. Nucleic acids having a double stranded region can include a first strand comprising P1001R (SEQ ID NO:3) or P1001R-A (SEQ ID NO:6 and a second strand comprising a variant of C1001R (SEQ ID NO:4)), wherein the variant comprises one or more substitutions. Nucleic acids having a double stranded region can include a first strand comprising P1002F (SEQ ID NO:7) or P1002F-A (SEQ ID NO:11) and a second strand comprising a variant of C1002F (SEQ ID NO:8), wherein the variant comprises one or more substitutions. Nucleic acids having a double stranded region can include a first strand comprising P1002R (SEQ ID NO:9) or P1002R-A (SEQ ID NO:12) and a second strand comprising a variant of C1002R (SEQ ID NO:10), wherein the variant comprises one or more substitutions. Optionally, the variant comprises at most 4, 3, 2 or 1 substitutions.

Figure 2:
FIG. 2 is a schematic showing an adapter of SEQ ID NO:1 (P1001F), SEQ ID NO:3 (P1001R) and SEQ ID NO:4 (C1001R) located on both sides of a nucleic acid fragment from, for example, a nucleic acid sample isolated from genomic DNA.

As shown in FIG. 2, the isolated nucleic acids can be connected together to form adapters and/or primers or primer binding sites. Thus, isolated nucleic acids can include any one of SEQ ID NOs:1-15 or their complement connected to any one of SEQ ID NOs:1-15 or their complement. For example, SEQ ID NO:1 or complement thereof can be connected to SEQ ID NO:3 or its complement or variant thereof, e.g., SEQ ID NOs:13, 14, or 15.

Nucleic acids that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used herein. Nucleic acid primers, probes or templates can be DNA, RNA or analogs thereof.

A nucleic acid may be single stranded or double stranded. Optionally, double stranded nucleic acids are advantageous as they minimize secondary structures that may hinder nucleic acid synthesis. A double stranded nucleic acid may possess a single-stranded nick or a gap. Where double-stranded, a nucleic acid molecule can be blunt-ended, have an overhang or have a "sticky-end." Such nucleic acid molecules can be produced by any chemical or enzymatic method known in the art. Examples of such methods include phosphoramidite synthesis or replication in vivo or in vitro. A nucleic acid of the present disclosure can be linear (e.g. having free 3' and 5' ends) or it can be circular (e.g. lacking 5' and 3' ends).

Deoxyribonucleic acid (DNA) is a particularly useful nucleic acid. A particularly useful DNA is a single- or double-stranded deoxyribonucleic acid that contains a nucleotide sequence provided herein. The deoxyribonucleotides are typically joined by phosphodiester bonds, although in some cases, nucleic acid analogs are included that may have alternate backbones, such as, phosphoramide (e.g. Beaucage, et al., *Tetrahedron*, 49 (10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (e.g. Mag, et al., *Nucleic Acids Res.*, 19:1437 (1991); and U.S. Pat. No. 5,644,048), phosphorodithioate (e.g. Briu, et al., *J. Am. Chem. Soc.*, 111:2321 (1989)), O-methylphophoroamidite linkages (e.g. Eckstein, *Oligonucleotides and Analogues: A Practical Approach*, Oxford University Press), and peptide nucleic acid backbones and linkages (e.g. Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996)). Other analog nucleic acids include those with positive backbones (e.g. Denpcy, et al., *Proc, Natl. Acad. Sci. USA*, 92:6097 (1995)); non-ionic backbones (e.g. U.S. Pat. Nos. 5,386,023; 5,637,684; 5,602,240; 5,216,141; and 4,469,863; Kiedrowshi, et al., *Angew. Chem. Intl. Ed.* English, 30:423 (1991); Letsinger, et al., *J. Am. Chem. Soc.*, 110:4470 (1988); Letsinger, et al., *Nucleosides & Nucleotides*, 13:1597 (1994); Chapters 2 and 3, *ASC Symposium Series* 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); *Tetrahedron Lett.*, 37:743 (1996)) and non-ribose backbones, including for example, those described in U.S. Pat. Nos. 5,235,033 and 5,034,506, and Chapters 6 and 7, *ASC Symposium Series* 580, "Carbohydrate Modifications in Antisense Research", Ed. Y. S. Sanghui and P. Dan Cook. Nucleic acids containing one or more carbocyclic sugars are also included within the definition of nucleic acids (e.g. Jenkins, et al., *Chem. Soc. Rev.*, (1995) pp. 169 176). Several nucleic acid analogs are described in Rawls, C & E News, Jun. 2, 1997, page 35. All of these references are hereby expressly incorporated by reference. These modifications of the ribose-phosphate backbone may be done to facilitate the addition of exogenous moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*. Nucleic acids can also be derived from a prokaryote such as a bacterium, *Escherichia coli*, staphylococci or *Mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference. Cells, tissues, biological fluids, proteins and other samples can be obtained from these organisms and detected using an apparatus or method set forth herein.

A nucleic acid can be obtained from a preparative method such as genome isolation, genome fragmentation, gene cloning and/or amplification. The nucleic acid can be obtained from an amplification technique such as polymerase chain reaction (PCR), rolling circle amplification (RCA), multiple displacement amplification (MDA) or the like. Amplification can also be carried out using a method set forth in Sambrook et al., *Molecular Cloning: A Laboratory Manual, 3rd edition*, Cold Spring Harbor Laboratory, New York (2001) or in Ausubel et al., *Current Protocols in Molecular Biology*, John Wiley and Sons, Baltimore, Md. (1998), each of which is incorporated herein by reference.

A nucleic acid molecule that includes the sequence or the complement of any one of SEQ ID NOs:1-12 can include a linker moiety that is exogenous to the nucleic acid. Any of a variety of linker moieties can be used. Optionally, the linker moiety does not contain a nucleotide or nucleic acid moiety. A linker moiety can be attached to a nucleic acid strand via any of a variety of chemistries known in the art. For example, a linker moiety can be attached to the 3' position of the nucleotide at the 3' end of a nucleic acid strand, a linker moiety can be attached to the 5' position of the nucleotide at the 5' end of a nucleic acid strand, a linker moiety can be attached to a phosphate moiety in the backbone of a nucleic acid strand or a linker moiety can be attached to a base moiety of a nucleic acid strand. A linker can be relatively stable to conditions to which a nucleic acid strand will be subjected. Alternatively, a linker used in a nucleic acid of the present disclosure can be cleavable, for example, using a reagent or physical manipulation to which the nucleic acid is subjected. For example, a linker can be cleaved to remove a label that was attached to a nucleic acid strand via the linker. Similarly, a nucleic acid can be removed from a solid phase support by cleaving a linker that mediates attachment of the nucleic acid to the solid phase support.

Optionally, the nucleic acid molecule can include a label moiety. Optionally, a linker moiety can attach a label moiety to a nucleic acid. Typically, the label moiety is exogenous to the nucleic acid. Examples of useful exogenous labels include, but are not limited to, radiolabel moieties, luminophore moieties, fluorophore moieties, quantum dot moieties, chromophore moieties, enzyme moieties, electromagnetic spin labeled moieties, nanoparticle light scattering moieties, and any of a variety of other signal generating moieties known in the art. Suitable enzyme moieties include, for example, horseradish peroxidase, alkaline phosphatase, beta-galactosidase, or acetylcholinesterase. Exemplary fluorophore labels include, but are not limited to rhodols; resorufins; coumarins; xanthenes; acridines; fluoresceins; rhodamines; erythrins; cyanins; phthalaldehydes; naphthylamines; fluorescamines; benzoxadiazoles; stilbenes; pyrenes; indoles; borapolyazaindacenes; quinazolinones; eosin; erythrosin; Malachite green; CY dyes (GE Biosciences), including Cy3 (and its derivatives), Cy5 (and its derivatives) and Cy7 (and its derivatives); DYOMICS and DYLIGHT dyes (Dyomics) including DY-547, DY-630, DY-631, DY-632, DY-633, DY-634, DY-635, DY-647, DY-649, DY-652, DY-678, DY-680, DY-682, DY-701, DY-734, DY-752, DY-777 and DY-782; Lucifer Yellow; CASCADE BLUE; TEXAS RED; BODIPY (boron-dipyrromethene) (Molecular Probes) dyes including BODIPY 630/650 and BODIPY 650/670; ATTO dyes (Atto-Tec) including ATTO 390, ATTO 425, ATTO 465, ATTO 610 611X, ATTO 610, ATTO 635; ALEXA FLUORS including ALEXA FLUOR 633, ALEXA FLUOR 647, ALEXA FLUOR 660, ALEXA FLUOR 700, ALEXA FLUOR 750, and ALEXA FLUOR 680 (Molecular Probes); DDAO (7-hydroxy-9H-(1,3-dichloro-9,9-dimethylacridin-2-one or any derivatives thereof) (Molecular Probes); QUASAR dyes (Biosearch); IRDYES dyes (LiCor) including IRDYE 700DX (NHS ester), IRDYE 800RS (NHS ester) and IRDYE 800CW (NHS ester); EVOBLUE dyes (Evotech Biosystems); JODA 4 dyes (Applied Biosystems); HILYTE dyes (AnaSpec); MR121 and MR200 dyes (Roche); Hoechst dyes 33258 and 33242 (Invitrogen); FAIR OAKS RED (Molecular Devices); SUNNYVALE RED (Molecular Devices); LIGHT CYCLER RED (Roche); EPOCH (Glen Research) dyes including EPOCH REDMOND RED, EPOCH YAKIMA YELLOW, EPOCH GIG HARBOR GREEN; Tokyo green (M. Kamiya, et al., 2005 *Angew. Chem. Int. Ed.* 44:5439-5441); and CF dyes including CF 647 and CF555 (Biotium), and others known in the art such as those described in *Principles of Fluorescence Spectroscopy*, Joseph R. Lakowicz (Editor), Plenum Pub Corp, 2nd edition (July 1999) and the 6th Edition of *Molecular Probes Handbook* by Richard P. Hoagland.

A secondary label can be used with the provided nucleic acid molecules or methods of the present disclosure. A secondary label is a binding moiety that can bind specifically to a partner moiety. For example, a ligand moiety can be attached to a nucleic acid or nucleotide to allow capture or detection via specific affinity of the ligand for a receptor. Exemplary pairs of binding moieties that can be used include, without limitation, antigen and immunoglobulin or active fragments thereof, such as a Fab, Fab', F(ab')2, Fv, or single chain Fv (scFv; immunoglobulin and immunoglobulin (or active fragments, respectively); avidin and biotin, or analogs thereof having specificity for avidin; streptavidin and biotin, or analogs thereof having specificity for streptavidin; or carbohydrates and lectins.

Optionally, the secondary label can be a chemically modifiable moiety. Optionally, labels having reactive functional groups can be incorporated into a nucleic acid. Subsequently, the functional group can be covalently reacted with a primary label moiety. Suitable functional groups include, but are not limited to, amino groups, carboxy groups, maleimide groups, oxo groups, organic azide groups, monosubstituted alkyne groups and thiol groups.

Optionally, a linker moiety can attach a nucleic acid to a solid phase support. The solid support can be made from any of a variety of materials used for analytical biochemistry. Suitable materials may include glass, polymeric materials, silicon, quartz (fused silica), borofloat glass, silica, silica-based materials, carbon, metals, an optical fiber or bundle of optical fibers, sapphire, or plastic materials. The particular material can be selected based on properties desired for a particular use. For example, materials that are transparent to a desired wavelength of radiation are useful for analytical techniques that will utilize radiation of that wavelength. Conversely, it may be desirable to select a material that does not pass radiation of a certain wavelength (e.g. being opaque, absorptive or reflective). Other properties of a material that can be exploited are inertness or reactivity to certain reagents used in a downstream process, such as those set forth herein, or ease of manipulation, or low cost of manufacture.

A particularly useful solid support is a particle such as a bead or microsphere. Populations of beads can be used for attachment of populations of nucleic acids. In some embodiments, it may be useful to use a configuration whereby each bead has a single type of nucleic acid. Alternatively, different types of nucleic acids need not be separated on a bead-by-bead basis. As such, a single bead can bear multiple different types of nucleic acids. The composition of a bead can vary, depending for example, on the format, chemistry and/or method of attachment to be used. Exemplary bead compositions include solid supports, and chemical functionalities imparted thereto, used in protein and nucleic acid capture methods. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as other materials set forth in "Microsphere Detection Guide" from Bangs Laboratories, Fishers Ind., which is incorporated herein by reference.

The geometry of a particle, bead or microsphere also can correspond to a wide variety of different forms and shapes. For example, they can be symmetrically shaped (e.g. spherical or cylindrical) or irregularly shaped (e.g. controlled pore glass). In addition, beads can be porous, thus increasing the surface area available for capture of nucleic acids or other components. Exemplary sizes for beads used herein can range from nanometers to millimeters or from about 10 nm-1 mm.

Optionally, beads can be arrayed or otherwise spatially distinguished. Exemplary bead-based arrays that can be used include, without limitation, a BeadChip™ Array available from Illumina, Inc. (San Diego, Calif.) or arrays such as those described in U.S. Pat. No. 6,266,459; 6,355,431; 6,770,441; 6,859,570; or 7,622,294; or PCT Publication No. WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. Pat. App. Pub. Nos. 2004/0263923 A1, 2004/0233485 A1, 2004/0132205 A1, or 2004/0125424 A1, each of which is incorporated herein by reference.

As will be recognized from the above bead array embodiments, a method or composition of the present disclosure can be configured in a multiplex format whereby multiple different types of nucleic acids are manipulated or detected in parallel. A composition or method of the present disclosure can include at least 2, 10, 100, $1 \times 10^3$, $1 \times 10^4$, $1 \times 10^5$, $1 \times 10^6$, $1 \times 10^9$, or more different nucleic acids. Alternatively or additionally, a composition or method of the present disclosure can include at most $1 \times 10^9$, $1 \times 10^6$, $1 \times 10^5$, $1 \times 10^4$, $1 \times 10^3$, 100, 10, 2 or fewer, different nucleic acids.

Further examples of commercially available arrays that can be used include, for example, an Affymetrix GeneChip™ array. A spotted array can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful arrays include those that are used in nucleic acid sequencing applications. For example, arrays that are used to attach amplicons of genomic fragments (often referred to as clusters) can be particularly useful. Examples of nucleic acid sequencing arrays that can be used herein include those described in Bentley et al., *Nature* 456:53-59 (2008), PCT Pub. Nos. WO 91/06678; WO 04/018497 or WO 07/123744; U.S. Pat. No. 7,057,026; 7,211,414; 7,315,019; 7,329,492 or 7,405,281; or U.S. Pat. App. Pub. No. 2008/0108082, each of which is incorporated herein by reference.

A nucleic acid can be attached to a support in a way that provides detection at a single molecule level or at an ensemble level. For example, a plurality of different nucleic acids can be attached to a solid support in a way that an individual nucleic acid molecule on the support can be distinguished from all neighboring nucleic acid molecules of the support. As such, one or more different nucleic acids can be attached to a solid support in a format where each single nucleic acid molecule is physically isolated and detected in a way that the single molecule is resolved from all other molecules on the solid support.

Optionally, SEQ ID NOs:1-12 can be employed in one or more nucleic acid ensembles, an ensemble being a population of nucleic acids having a common template sequence. SEQ ID NOs:1-12 can be located on the 3' side, the 5' side or both 3' and 5' sides of the common template sequence. Cluster methods can be used to attach one or more ensembles to a solid support. As such, an array can have a plurality of ensembles, each of the ensembles being referred to as a cluster or array feature in that format. Clusters can be formed using methods known in the art such as bridge amplification or emulsion PCR. Useful bridge amplification methods are described, for example, in U.S. Pat. No. 5,641,658 or 7,115,400; or U.S. Patent Pub. Nos. 2002/0055100 A1; 2004/0002090 A1; 2004/0096853 A1; 2007/0128624 A1; or 2008/0009420 A1. Emulsion PCR methods include, for example, methods described in Dressman et al., *Proc. Natl. Acad. Sci. USA* 100:8817-8822 (2003), WO 05/010145, or U.S. Patent Pub. Nos. 2005/0130173 A1 or 2005/0064460 A1, each of which is incorporated herein by reference in its entirety. Another useful method for amplifying nucleic acids on a surface is rolling circle amplification (RCA), for example, as described in Lizardi et al., *Nat. Genet.* 19:225-232 (1998) or US 2007/0099208 A1, each of which is incorporated herein by reference.

Optionally, a solid phase support is present on or in a flow cell. A flow cell allows convenient fluidic manipulation by passing solutions into and out of a fluidic chamber that contacts the support-bound, nucleic acid molecule. The flow cell also provides for detection of the nucleic acid molecule. For example, a detector can be positioned to detect signals from the solid support, such as signals from a label that is recruited to a nucleic acid on the solid support. Exemplary flow cells that can be used are described, for example, in US Pat. App. Pub. No. 2010/0111768 A1, WO 05/065814 or US Pat. App. Pub. No. 2012/0270305 A1, each of which is incorporated herein by reference.

A nucleic acid of the present disclosure need not be attached to a solid support. Moreover, a method that employs a nucleic acid set forth herein need not employ a solid phase support. Rather, a nucleic acid of the present disclosure can be present in solution phase. Similarly, a method that employs a nucleic acid set forth herein can be carried out in solution. In some methods, a nucleic acid of the present disclosure can be attached to a solid phase for one or more of the steps in the method and the nucleic acid can be in solution for another one or more steps in the method. In configurations in which the nucleic acid functions as a reagent or product in a method, a reagent used to produce the nucleic acid, or a product derived from the nucleic acid, can be attached to a solid phase support for some steps of the method and the reagent or product can be in solution phase for other steps of the method.

Exemplary Adapter Pairs

The present disclosure provides nucleic acids having two regions of non-naturally occurring sequence. Such nucleic acid constructs can be useful for amplifying a template region that intervenes the two regions of non-naturally occurring sequence. For example, the non-naturally occurring sequence regions and their complements can function as adapters that form primer binding sites for primers used in amplification techniques such as polymerase chain reaction (PCR).

A particularly useful pair of adapters is provided by the P1001F (SEQ ID NO:1) and P1001R (SEQ ID NO:3) and their complementary sequences, C1001F (SEQ ID NO:2) and C1001R (SEQ ID NO:4), respectively. Accordingly, an isolated nucleic acid molecule of the present disclosure can include the sequence or the complement of SEQ ID NO:1 and the isolated nucleic acid molecule can further include the sequence or the complement of SEQ ID NO:3. The isolated nucleic acid molecule can be double stranded, in which case the sequence can include the sequence of SEQ ID NO:1, the sequence of SEQ ID NO:2, the sequence of SEQ ID NO:3, and the sequence of SEQ ID NO:4. The P1001F (SEQ ID NO:1) and P1001R (SEQ ID NO:3) sequences can, optionally, be replaced by the P1001F-A (SEQ ID NO:5) and/or P1001R-A (SEQ ID NO:6) sequences, respectively, in these constructs. Optionally, the adapter sequences flank a template region that is to be amplified or detected.

Another useful pair of adapters is provided by the P1002F (SEQ ID NO:7) and P1002R (SEQ ID NO:9) and their complementary sequences, C1002F (SEQ ID NO:8) and C1002R (SEQ ID NO:10), respectively. Accordingly, an isolated nucleic acid molecule of the present disclosure can include the sequence or the complement of SEQ ID NO:7 and the isolated nucleic acid molecule can further include the sequence or the complement of SEQ ID NO:9. The isolated nucleic acid molecule can be double stranded, in which case the sequence can include the sequence of SEQ ID NO:7, the sequence of SEQ ID NO:8, the sequence of SEQ ID NO:9, and the sequence of SEQ ID NO:10. The P1002F (SEQ ID NO:7) and P1002R (SEQ ID NO:9) sequences can, optionally, be replaced by the P1002F-A (SEQ ID NO:11) and/or P1002R-A (SEQ ID NO:12) sequences, respectively, in these constructs. Optionally, the adapter sequences flank a template region that is to be amplified or detected.

Exemplary Nucleic Acid populations

The present disclosure provides non-naturally occurring sequences that can be used for universal adapters, universal probes, universal priming sites or universal primers to manipulate or detect complex mixtures of nucleic acid templates. For example, a nucleic acid sample having high sequence complexity can be captured, replicated, amplified or detected based on hybridization between nucleic acids having complementary, universal sequences. Because the sequences set forth herein have been designed for absence of substantial complementarity to native genome sequences, the designed sequences can provide a specific and robust means for multiplex capture, replication, amplification and/ or detection of a complex mixture of templates that have been modified to include the sequences. For example, the non-naturally occurring sequence regions and their complements can function as adapters that form primer binding sites for primers used in amplification techniques such as polymerase chain reaction (PCR).

Accordingly, the present disclosure further provides a population of different nucleic acid molecules. The population of different nucleic acid molecules can include a plurality of nucleic acid molecules, wherein each of the nucleic acid molecules includes a universal sequence region and a variable sequence region, wherein the sequence of the variable sequence region differs between different nucleic acid molecules in the population, wherein the sequence of the universal sequence region is the same for the nucleic acid molecules in the population, and wherein the universal sequence region includes the sequence or the complement of any one of SEQ ID NOs:1-12. The population of different nucleic acid molecules can include one or more subsets, populations or groups of nucleic acid molecules, each of the subsets, populations, or groups can have different variable regions while the variable region of each nucleic acid molecule can be the same. By way of example, the population of different nucleic acid molecules can comprise a first subset of nucleic acid molecules comprising a first variable region and a second subset of nucleic acid molecules having a second variable region. The population of different nucleic acid molecules can comprise a plurality of subsets of nucleic acid molecules wherein each subset of nucleic acid molecules comprises the same variable region and wherein each subset has a different variable region from another subset of nucleic acid molecules.

Provided is a population of different nucleic acid molecules, comprising a plurality of nucleic acid molecules, wherein each of the nucleic acid molecules comprises a universal sequence region and a variable sequence region, wherein the sequence of the variable sequence region differs between different nucleic acid molecules in the population, wherein the sequence of the universal sequence region is the same for the nucleic acid molecules in the population, and wherein the universal sequence region comprises the sequence or the complement of SEQ ID NO:1, SEQ ID NO:2, SEQ ID NO:7, or SEQ ID NO:8. The universal sequence region can be located 5' relative to the location of the variable sequence region in a strand of each of the different nucleic acid molecules. Optionally, the universal sequence region is located 3' relative to the location of the variable sequence region in a strand of each of the different nucleic acid molecules. The nucleic acid molecules can be single stranded or double stranded, thereby having a first strand and a second strand. If the nucleic acid molecules are double-stranded, the first strand of each of the nucleic acid molecules can include the sequence of SEQ ID NO:1, SEQ ID NO:2, SEQ ID NO:7, or SEQ ID NO:8 and the second strand of each of the nucleic acid molecules can include the complement of SEQ ID NO:1, SEQ ID NO:2, SEQ ID NO:7, or SEQ ID NO:8. Optionally, the nucleic acid molecules are attached to sites in an array of nucleic acids. Optionally, each of the sites in the array of nucleic acids is attached to an ensemble of nucleic acid molecules having the same sequence at the variable sequence region. Optionally, each of the sites in the array of nucleic acids is attached to a single nucleic acid molecule.

The nucleic acid molecules can be attached to label moieties, the labels moieties being exogenous to the nucleic acids. Optionally, the nucleic acid molecules are in solution phase.

Each of the nucleic acid molecules in the population can also include a second universal sequence region, wherein the sequence of the second universal sequence region is the same for the nucleic acid molecules in the population. The sequence of the second universal sequence region can be the sequence or the complement of SEQ ID NO:3, SEQ ID NO:4, SEQ ID NO:9, or SEQ ID NO:10. Optionally, the variable sequence region is located between the universal sequence region and the second universal sequence region in a strand of each of the different nucleic acid molecules. Optionally, a first strand of each of the nucleic acid molecules comprises the sequence of SEQ ID NO:3, SEQ ID NO:4, SEQ ID NO:9, or SEQ ID NO:10 and wherein the second strand of each of the nucleic acid molecules comprises the complement of SEQ ID NO:3, SEQ ID NO:4, SEQ ID NO:9, or SEQ ID NO:10. Optionally, the first strand of each of the nucleic acid molecules comprises the sequence of SEQ ID NO:1, SEQ ID NO:2, SEQ ID NO:7, or SEQ ID NO:8 and wherein the second strand of each of the nucleic acid molecules comprises the complement of SEQ ID NO:1, SEQ ID NO:2, SEQ ID NO:7, or SEQ ID NO:8. Optionally, the first strand of each of the nucleic acid molecules comprises the complement of SEQ ID NO:1, SEQ ID NO:2, SEQ ID NO:7, or SEQ ID NO:8 and wherein the second strand of each of the nucleic acid molecules comprises the sequence of SEQ ID NO:1, SEQ ID NO:2, SEQ ID NO:7, or SEQ ID NO:8. Optionally, the sequence complexity for the nucleic acid molecules in the population is at least 25% of the complexity of a human genome. Optionally, the sequences of the variable sequence regions are at least 100 nucleotides in length. Optionally, the sequences of the variable sequence regions comprise human genome sequence fragments.

Optionally, the universal sequence region is positioned to provide a binding site for a primer that is used to copy, amplify or detect a variable region. Accordingly, the universal sequence region can be located 5' relative to the location of the variable sequence region in a strand of each of the different nucleic acid molecules. Alternatively, the universal sequence region can be located 3' relative to the location of the variable sequence region in a strand of each of the different nucleic acid molecules. In some configurations, each of the nucleic acid molecules in a population can include a first universal sequence region and a second universal sequence region, wherein the sequence of the respective universal sequence regions is the same for the nucleic acid molecules in the population. Optionally, the variable sequence region can be located between the universal sequence region and the second universal sequence region in a strand of each of the different nucleic acid molecules of a population. Configurations that employ two different universal sequence regions can employ the pairs of sequences and/or partner sequences set forth previously herein.

One or more of the nucleic acid molecules in a population of different nucleic acids can include a linker moiety. The linker moiety can be used to attach the nucleic acids to a label, solid phase support or other entity. For example, nucleic acid molecules can be attached to sites in an array of nucleic acids. In particular configurations, each site of the array is attached to one type of nucleic acid molecule in the population. More specifically, each site can attach a single nucleic acid having a particular variable region sequence. Alternatively, each site can attach a plurality of nucleic acid molecules, wherein substantially all of the nucleic acid molecules that are attached to a particular site have the same sequence for the variable region. In this latter example, the site can be attached to both strands of a double stranded nucleic acid such that strands containing the variable sequence region and its complement are both attached to the site.

A population of nucleic acid molecules can include members having any of a variety of sequence lengths. A population can include a relatively large variance in sequence length among its member nucleic acids. Alternatively, the population can have a small variance in sequence length among its members. In some configurations, the average length for the variable sequence region can be at least 100, 250, 500, $1 \times 10^3$, $1 \times 10^4$, $1 \times 10^6$, or more nucleotides. Alternatively or additionally, the average length for the variable sequence regions in the population can be at most $1 \times 10^6$, $1 \times 10^4$, $1 \times 10^3$, 500, 100, 250, or fewer nucleotides. A population of nucleic acids can be characterized according to the minimum length of the variable sequence regions among its members. For example, the minimum length can be at least 100, 250, 500, $1 \times 10^3$, $1 \times 10^4$, $1 \times 10^6$, or more nucleotides. Alternatively or additionally, a population of nucleic acids can be characterized according to the maximum length of the variable sequence regions among its members. For example, the maximum length can be at most $1 \times 10^6$, $1 \times 10^4$, $1 \times 10^3$, 500, 100, 250, or fewer nucleotides.

A population of nucleic acid molecules can include variable regions that collectively cover any of a variety of sequence complexities. For many applications of the compositions set forth herein, the maximum sequence complexity for the collective variable regions will be a function of the complexity of the genome from which the population is derived. For example, the sequence complexity for the variable regions of a population of nucleic acids can be at most the complexity of a genome set forth herein or known in the art. However, a population of nucleic acid molecules can have substantially lower sequence complexity compared to the sequence complexity of a particular genome. For example, the sequence complexity for the collective variable regions in a population can be at least 10%, 25%, 50%, 75%, 90% or more of the complexity of a genome set forth herein or known in the art. Alternatively or additionally, the sequence complexity for the collective variable regions in a population can be at most 90%, 75%, 50%, 25%, 10% or less of the complexity of a genome set forth herein or known in the art.

Exemplary Methods

The present disclosure provides a method for preparing a nucleic acid library. The method can include steps of attaching universal adapters to nucleic acid fragments from a genome, thereby producing a library of nucleic acid molecules, wherein each of the nucleic acid molecules in the library includes: (i) a variable sequence region that differs between the nucleic acid molecules in the library, and (ii) a universal sequence region that is the same for the nucleic acid molecules in the library, wherein the universal sequence region comprises the sequence or the complement of any one of SEQ ID Nos:1-12. Optionally, the method can further include attaching second universal adapters to the nucleic acid fragments from the genome, whereby each of the nucleic acid molecules in the library includes: (i) the variable sequence region that differs between the nucleic acid molecules in the library, (ii) the universal sequence region that is the same for the nucleic acid molecules in the library, wherein the universal sequence region includes the sequence or the complement of any one of SEQ ID Nos:1-12, and (iii) a second universal sequence region that is the same for the nucleic acid molecules in the library, wherein the second universal sequence region includes the sequence or the complement of any one of SEQ ID Nos:1-12.

For example, provided is a method for preparing a nucleic acid library, comprising attaching universal adapters to nucleic acid fragments from a genome, thereby producing a library of nucleic acid molecules, wherein each of the nucleic acid molecules in the library comprises: (i) a variable sequence region that differs between the nucleic acid molecules in the library, and (ii) a universal sequence region that is the same for the nucleic acid molecules in the library, wherein the universal sequence region comprises the sequence or the complement of SEQ ID NO:1, SEQ ID NO:2, SEQ ID NO:7, or SEQ ID NO:8. The attaching can include ligating the universal adapters to the nucleic acid fragments from the genome. Optionally, the attaching comprises amplifying regions of the genome using primers that comprise the universal sequence, thereby producing amplicons comprising a variable sequence region from the genome and the universal sequence from the primers.

The method can also include amplifying the nucleic acid molecules in the library using a universal primer that comprises the sequence or the complement of SEQ ID NO:1, SEQ ID NO:2, SEQ ID NO:7, or SEQ ID NO:8. Optionally, the universal primer is attached to a solid phase support, whereby the amplifying produces amplicons of the library that are attached to the solid phase support. Optionally, the universal primer is attached to a label moiety, whereby the amplifying produces amplicons of the library that are attached to the label moiety.

As described herein, the method can also include attaching second universal adapters to the nucleic acid fragments from the genome, whereby each of the nucleic acid molecules in the library comprises: (i) the variable sequence region that differs between the nucleic acid molecules in the library, (ii) the universal sequence region that is the same for the nucleic acid molecules in the library, wherein the universal sequence region comprises the sequence or the complement of SEQ ID NO:1, SEQ ID NO:2, SEQ ID NO:7, or SEQ ID NO:8 and (iii) a second universal sequence region that is the same for the nucleic acid molecules in the library, wherein the second universal sequence region comprises the sequence or the complement of SEQ ID NO:3, SEQ ID NO:4, SEQ ID NO:9, or SEQ ID NO:10.

The variable sequence region can be located between the universal sequence region and the second universal sequence region in a strand of each of the nucleic acid molecules in the library.

The method can also include amplifying the nucleic acid molecules in the library using a universal primer that comprises the sequence or the complement of SEQ ID NO:1, SEQ ID NO:2, SEQ ID NO:7, or SEQ ID NO:8 and using a second universal primer that comprises the sequence or the complement of SEQ ID NO:3, SEQ ID NO:4, SEQ ID NO:9, or SEQ ID NO:10. Optionally, one or both of the universal primer and the second universal primer is attached to a solid phase support, whereby the amplifying produces amplicons of the library that are attached to the solid phase support. Optionally, one or both of the universal primer and the second universal primer is attached to a label moiety, whereby the amplifying produces amplicons of the library that are attached to the label moiety.

The method can also include capturing the nucleic acid molecules in the library by hybridizing a universal capture probe to the universal sequence region. Optionally, the universal capture probe is attached to a solid phase support.

Universal adapters can be attached to nucleic acids using any of a variety of methods. For example, the universal adapters can be ligated to a population of genomic DNA fragments. Ligation can be mediated by nucleic acid enzymes known in the art such as ligase enzymes or transposases. Exemplary protocols for use of ligases are set forth, for example, in Sambrook et al., *Molecular Cloning: A Laboratory Manual,* 3rd edition, Cold Spring Harbor Laboratory, New York (2001) or in Ausubel et al., *Current Protocols in Molecular Biology,* John Wiley and Sons, Baltimore, Md. (1998), each of which is incorporated herein by reference. Exemplary methods that employ a transposase enzyme for ligation include, but are not limited to, those set forth in US Pat. App. Pub. Nos. 2019/0048332 A1; 2018/0201925 A1; 2018/0016571 A1; 2016/0251650 A1; 2015/0368638 A1; 2015/0176071 A1; or 2010/0120098 A1, each of which is incorporated herein by reference.

Another method that can be employed to attach universal adapters to nucleic acids is to copy or amplify regions of a genome (or other nucleic acid sample) using primers that comprise the universal adapter sequence. The resulting copies or amplicons will include a variable sequence region from the genome and the universal sequence from the primers. The primers used for this amplification step can be configured to have a 3' region that hybridizes to genome regions of interest, such that extension of the 3' end will produce a copy of the genome region, and the primers can further include a region that has the universal sequence. Generally, the universal sequence will be located to the 5' side of the 3' region that hybridizes to genome regions of interest in the primer. As such, the universal sequence will be positioned to provide a universal primer binding site for subsequent copying, amplification or sequencing of the copy of the genome region.

A method of the present disclosure can include a step of amplifying nucleic acid molecules in a library using a universal primer that includes the sequence or the complement of any one of SEQ ID Nos:1-12. The universal primer can be in solution phase or, alternatively, the universal primer can be attached to a solid phase support. A universal primer can be attached to a solid phase support in a way that allows the 3' end of the universal primer to be extended in order to copy or amplify a template nucleic acid. As such, amplification or copying of a nucleic acid template using a solid phase primer can be used to produce amplicons that are in turn attached to the solid support. For some configurations, two different universal primers are attached to a solid support and used to amplify the nucleic acids using bridge amplification. Amplicons resulting from bridge amplification can be attached to a surface via both strands.

A method of the present disclosure can include a step of amplifying nucleic acid molecules in a library using a universal primer that includes the sequence or the complement of any one of SEQ ID Nos:1-12, wherein the universal primer is attached to an exogenous label. A universal primer can be attached to a label in a way that allows the 3' end of the universal primer to be extended in order to copy or amplify a template nucleic acid. As such, amplification or copying of a nucleic acid template using a labeled primer can be used to produce amplicons that are in turn attached to the label.

Throughout this application various publications, patents and/or patent applications have been referenced. The disclosures of these documents in their entireties are hereby incorporated by reference in this application.

A number of embodiments have been described. Nevertheless, it will be understood that various modifications may be made. Accordingly, other embodiments are within the scope of the following claims.

EXAMPLES

Example 1. Isolated Nucleic Acids as Adapters and Primer Binding Sites

To test the sequences, 1000 ng of lambda gDNA was enzymatically sheared and four different versions of isolated nucleic acids were ligated onto the ends of each fragment (HyperPlus library prep kit). Version 1 included an adapter of SEQ ID NOs:1, 3 and 4 as shown in FIG. 2 wherein SEQ ID NO:1 serves as a primer binding site for a primer having SEQ ID NO:2. Version 2 included an adapter of SEQ ID NOs:1, 13 and 4 wherein SEQ ID NO:1 serves as a primer binding site for a primer having SEQ ID NO:2. Version 3 included an adapter of SEQ ID NOs:1, 14 and 4 wherein SEQ ID NO:1 serves as a primer binding site for a primer having SEQ ID NO:2. Version 4 included an adapter of SEQ ID NOs:1, 15 and 4 wherein SEQ ID NO:1 serves as a primer binding site for a primer having SEQ ID NO:2. SEQ ID NOs:13, 14 and 15 are located in the same position as SEQ ID NO:3 shown in FIG. 2. After each library was made, 12 ng was used for PCR using a primer comprising SEQ ID NO:2 connected to SEQ ID NO:3 to determine the efficiency of adapter ligation. The results are shown in FIG. 1. Lane A1 is ladder, lane B1 is sheared lambda DNA, lane C1 is version 1, lane D1 is version 2, lane E1 is version 4 and lane F1 is version 3. FIG. 1 shows all four versions were used successfully as adapters and primers/primer binding sites and can be useful for universally amplifying nucleic acid samples for use in biological assays such as sequencing.

Figure 3:
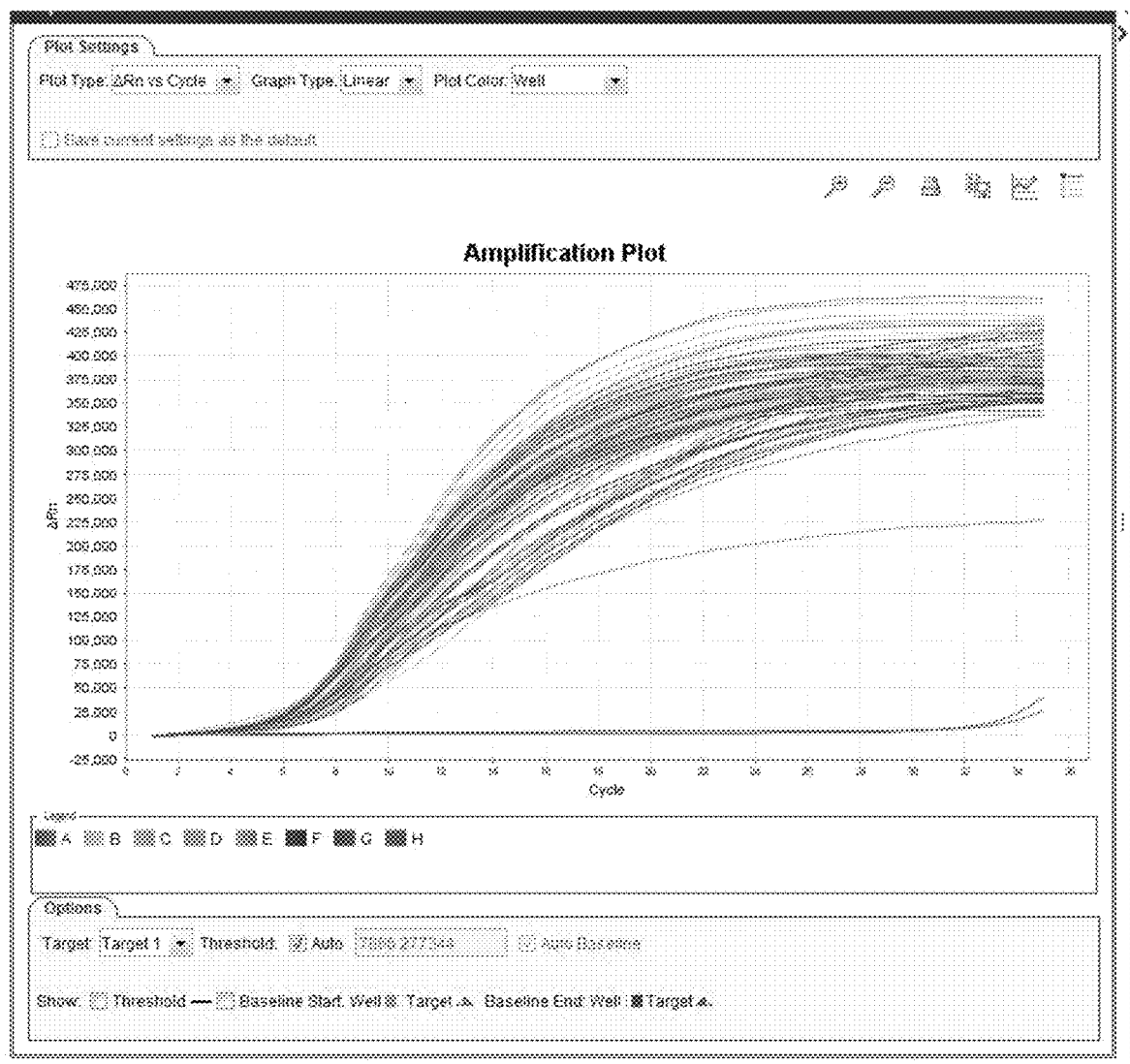
FIG. 3 plots the change in nucleic acid concentration per cycle for a PCR reaction that uses a pair of primers having SEQ ID NO:1 (P1001F) and SEQ ID NO:3 (P1001R), respectively to amplify template nucleic acids that are each flanked by the respective priming sites SEQ ID NO:2 (C1001F) and SEQ ID NO:4 (C1001R).

Example 2: Using Universal Primers to PCR Amplify Libraries of Different Templates Having Universal Priming Sites PCR amplification reactions were carried in a multiwell plate, each well containing a different template sequence. Each of the template sequences was flanked by universal priming sites having SEQ ID NO:2 and SEQ ID NO:4, respectively. The template in each well was amplified using universal primers having SEQ ID NO:1 and SEQ ID NO:3, respectively. The SEQ ID NO:3 primers were biotinylated on their 5' ends. PCR was carried out for 35 cycles. As shown in FIG. 3, use of the universal primers and universal priming sites yielded relatively uniform amplification rates and yields for the libraries across the wells.

Figure 4:
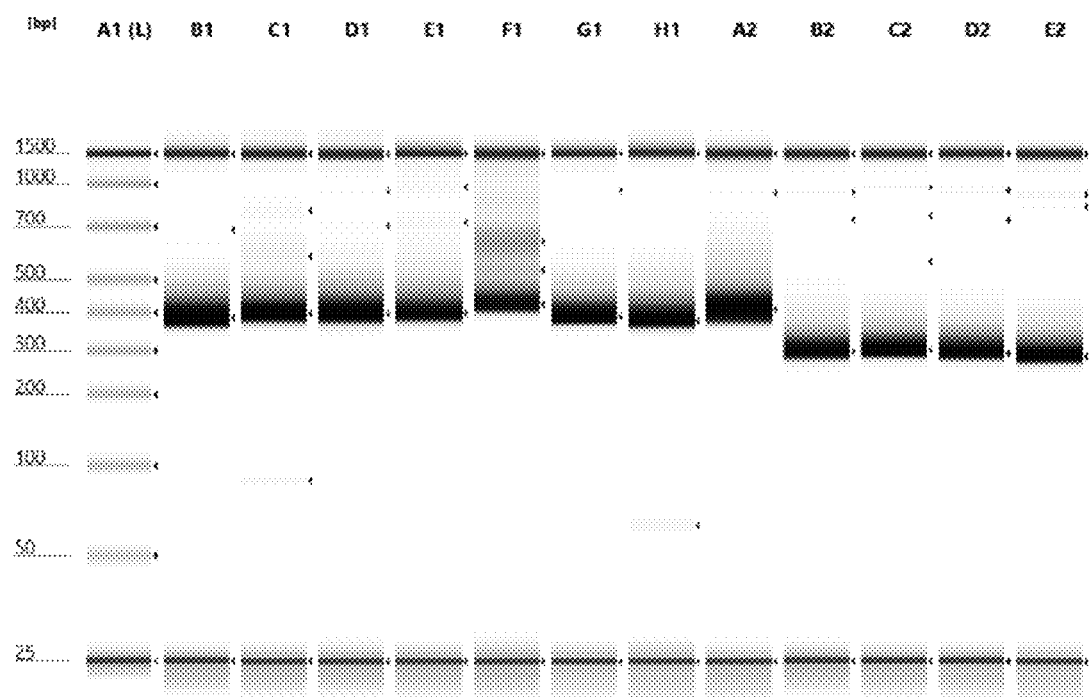
FIG. 4 shows an image from a Tapestation electrophoresis analysis in which a nucleic acid ladder (control) was loaded in lane A1, and amplicons produced from PCR reactions carried out on various templates are shown in lanes B1 through E2.

Amplicons produced in each of the wells were analyzed by electrophoresis on a Tapestation™ (Agilent, San Diego, Calif.). An aliquot of the amplicons produced in each well was loaded into lanes B1 through E2 of the Tapestation. As shown in FIG. 4, use of the universal primers and universal priming sites yielded libraries having uniform lengths of the expected size in each of the wells.

Example 3: Using a Universal Primer to Sequence a Library of PCR Amplicons Having Universal Priming Sites Flow cells were prepared for sequencing as follows. Amplicons were produced as set forth in Example 2 and independently bound to streptavidin-coated magnetic beads. This resulted in a population of 12 bead types, where each bead harbored a homogenous collection of template strands. The beads from the 12 reactions were pooled and attached to the inner surface of a flow cell. Next, sequencing primers having SEQ ID NO:1 were flowed into the flow cell and allowed to hybridize to the immobilized template strands.

Sequencing was performed cyclically, where each cycle included steps for (i) extension: adding a reversibly terminated nucleotide to the primers of the immobilized primer-template hybrids, (ii) examination: forming and detecting stabilized ternary complexes on the reversibly terminated, immobilized primer-template hybrids, and (iii) activation: cleaving the reversible terminator from the extended primers. Each cycle resulted in addition of a single nucleotide and detection of a subsequent nucleotide position. As such the number of cycles correlated directly with the length of the sequence read for each bead. Conditions for sequencing are set forth in US Pat. App. Pub. No. 2020/0032317 A1 and U.S. Pat. No. 10,710,076, each of which is incorporated herein by reference.

Figure 5:
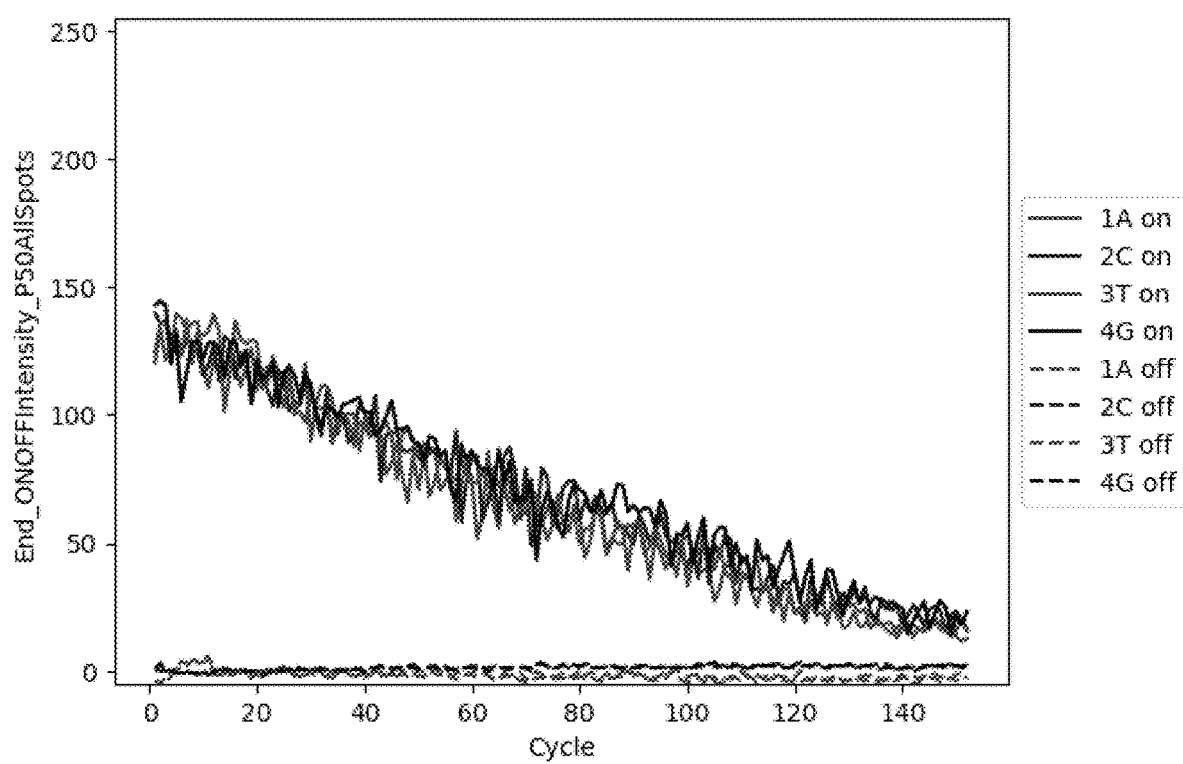
FIG. 5 shows plots of signal intensity vs. sequencing cycle for a 152 cycle sequencing run.

FIG. 5 shows plots of signal intensity vs. sequencing cycle for a 152 cycle sequencing run carried out using the flow cell that had been prepared as set forth above. Individual traces are shown for the 'on' intensity detected for each nucleotide type and for the 'off' intensity for each nucleotide type. For each bead in each cycle, the nucleotide type that produced the highest signal was identified as the 'on' signal and the other three nucleotide types were identified as the 'off' signal. The 'on' signals for each nucleotide type were averaged across all bead types detected in a given cycle, and the median intensity was plotted across all cycles to obtain each of the 'on' signal traces shown in the figure. Similar averaging of signal intensities across all bead types on a per cycle basis was used to arrive at the 'off' intensity traces shown in FIG. 5. The results of FIG. 5 demonstrated good separation between 'on' and 'off' intensities over the course of the 152 cycle run.

Signal decay for the 'on' traces was evaluated by fitting the traces to a curve defined by the following equation:

$$I = I_0 e^{-(n/\tau)} \quad \text{(Equation 1)}$$

wherein I is signal intensity, n is the number of cycles and τ is the cycle when the signal is about 37% of $I_0$ (initial signal intensity). Higher τ is indicative of reduced rate of signal decay, which is generally preferred since it indicates increased read length and sequencing accuracy. The goodness of fit was calculated as the coefficient of determination, $R^2$. Higher $R^2$ values correlate with reduced signal intensity variance over the sequencing run. The traces shown in FIG. 5 had an average τ of 74 and an average $R^2$ of 0.96.

Table 2 shows post processing results for the sequencing run. The first column shows the percent of the observed beads that are omitted from each analysis, where "PNN" includes all of the observed beads, P01 omits the lowest quality 1% of the data, P02 omits the lowest quality 2% of the data, etc. up to P06 which omits the lowest quality 6% of the data. For each row the number of "No Calls", "Right Calls" and "Wrong Calls" are shown along with the sum of those three columns shown under the "Total Calls" column. The percent of errors is shown along with the relevant Q score that was calculated for each value in the Q % column.

In nucleic acid sequencing applications, the Q score is a property that is logarithmically related to the base calling error probabilities (P) according to the following equation $$Q = -10 \log(P) \quad \text{(Equation 2)}$$

For example, a Q score of 20 (Q20) for a particular base call is equivalent to a 1 in 100 probability that the base call is incorrect. This means that the base call accuracy (i.e., the probability of a correct base call) is 99.0%. A higher base call accuracy of 99.9% is indicated by a Q score of Q30 and indicates an incorrect base call probability of 1 in 1000. Q40 indicates a base call accuracy of 99.99% (i.e. incorrect base call probability of 1 in 10,000), Q50 indicates an even higher base call accuracy of 99.999% (i.e. incorrect base call probability of 1 in 100,000), etc. Currently available high throughput sequencing platforms (i.e. 'next generation" sequencing platforms such as those available from Illumina, Inc., San Diego Calif.) typically use Q30 as a benchmark for quality. Higher Q scores are indicative of increased accuracy of variant calls, which provides increased accuracy of conclusions and reduced costs for validation experiments.

As indicated by the results of Table 2, when sequencing was carried out using universal primers having SEQ ID NO:1 and templates having universal priming sites having SEQ ID NO:2, a Q score of nearly Q46 was obtained without discarding any of the observed data. Omitting the lowest quality 1% of the data from the analysis yielded a Q score of Q64, far exceeding the currently accepted commercial benchmark of Q30.

TABLE 2

| Q % | NO CALLS | RIGHT CALLS | WRONG CALLS | TOTAL CALLS | ERROR PERCENT | Q SCORE |
|---|---|---|---|---|---|---|
| PNN | 320 | 2427399 | 64 | 2427463 | 0.002636 | 45.78973 |
| P00 | 0 | 2427399 | 64 | 2427463 | 0.002636 | 45.78973 |
| P01 | 0 | 2406031 | 1 | 2406032 | 4.16E−05 | 63.81301 |
| P02 | 0 | 2392010 | 0 | 2392010 | 0 | 70 |
| P03 | 0 | 2374491 | 0 | 2374491 | 0 | 70 |
| P04 | 0 | 2352627 | 0 | 2352627 | 0 | 70 |
| P05 | 0 | 2326175 | 0 | 2326175 | 0 | 70 |
| P06 | 0 | 2293780 | 0 | 2293780 | 0 | 70 |

What is claimed is:

1. A composition comprising an isolated nucleic acid molecule comprising the sequence or the complement of SEQ ID NO:1.

2. The composition of claim 1, wherein the 3' end of the sequence of SEQ ID NO:1 is the 3' end of a strand of the isolated nucleic acid molecule, or wherein the 3' end of the complement of SEQ ID NO:1 is the 3' end of a strand of the isolated nucleic acid molecule.

3. The composition of claim 1, wherein the isolated nucleic acid molecule is single stranded.

4. The composition of claim 1, wherein the isolated nucleic acid molecule is double stranded, thereby having a first strand and a second strand.

5. The composition of claim 4, wherein the first strand of the isolated nucleic acid molecule comprises the sequence of SEQ ID NO:1 and wherein the second strand of the isolated nucleic acid comprises the complement of SEQ ID NO:1.

6. The composition of claim 1, wherein the nucleic acid comprises DNA.

7. The composition of claim 1, wherein the nucleic acid comprises RNA.

8. The composition of claim 1, wherein the nucleic acid comprises a linker moiety, the linker moiety being exogenous to the nucleic acid.

9. The composition of claim 8, wherein the linker moiety attaches the nucleic acid to a label moiety, the label moiety being exogenous to the nucleic acid.

10. The composition of claim 8, wherein the exogenous linker moiety attaches the nucleic acid to a solid phase support.

11. The composition of claim 10, wherein the solid phase support comprises a bead.

12. The composition of claim 10, wherein the solid phase support comprises a site of a nucleic acid array.

13. The composition of claim 1, wherein the nucleic acid molecule is in solution phase.

14. The composition of claim 1, wherein the isolated nucleic acid molecule further comprises the sequence or the complement of SEQ ID NO:3.

15. The composition of claim 14, wherein the 3' end of the sequence of SEQ ID NO:3 is the 3' end of a strand of the isolated nucleic acid molecule, or wherein the 3' end of the complement of SEQ ID NO:3 is the 3' end of a strand of the isolated nucleic acid molecule.

16. The composition of claim 14, wherein the isolated nucleic acid molecule is double stranded, thereby having a first strand and a second strand.

17. The composition of claim 16, wherein the first strand of the isolated nucleic acid molecule comprises the sequence of SEQ ID NO:3 and wherein the second strand of the isolated nucleic acid comprises the complement of SEQ ID NO:3.

18. The composition of claim 17, wherein the first strand of each of the nucleic acid molecules comprises the sequence of SEQ ID NO:1 and wherein the second strand of each of the nucleic acid molecules comprises the complement of SEQ ID NO:1.

19. The composition of claim 17, wherein the first strand of each of the nucleic acid molecules comprises the complement of SEQ ID NO:1 and wherein the second strand of each of the nucleic acid molecules comprises the sequence of SEQ ID NO:1.

20. The composition of claim 1, wherein the isolated nucleic acid molecule further comprises a variant of SEQ ID NO:3 having 1, 2, 3 or 4 nucleotide substitutions.

21. The composition of claim 20, wherein the variant is SEQ ID NO:13, SEQ ID NO:14 or SEQ ID NO:15.

22. A population of different nucleic acid molecules, comprising a plurality of nucleic acid molecules,
   wherein each of the nucleic acid molecules comprises a universal sequence region and a variable sequence region,
   wherein the sequence of the variable sequence region differs between different nucleic acid molecules in the population,
   wherein the sequence of the universal sequence region is the same for the nucleic acid molecules in the population, and
   wherein the universal sequence region comprises the sequence or the complement of SEQ ID NO:1.

23. A method for preparing a nucleic acid library, comprising
   attaching universal adapters to nucleic acid fragments from a genome, thereby producing a library of nucleic acid molecules,
   wherein each of the nucleic acid molecules in the library comprises:
      (i) a variable sequence region that differs between the nucleic acid molecules in the library, and
      (ii) a universal sequence region that is the same for the nucleic acid molecules in the library, wherein the universal sequence region comprises the sequence or the complement of SEQ ID NO:1.

* * * * *

SEQUENCE LISTING

<160> NUMBER OF SEQ ID NOS: 15

<210> SEQ ID NO 1
<211> LENGTH: 32
<212> TYPE: DNA
<213> ORGANISM: Artificial Sequence
<220> FEATURE:
<223> OTHER INFORMATION: Synthetic Construct

<400> SEQUENCE: 1
acaggtcgcc gttgaggcta ccagcggaca ga                              32

<210> SEQ ID NO 2
<211> LENGTH: 32
<212> TYPE: DNA
<213> ORGANISM: Artificial Sequence
<220> FEATURE:
<223> OTHER INFORMATION: Synthetic Construct

<400> SEQUENCE: 2
tctgtccgct ggtagcctca acggcgacct gt                              32

<210> SEQ ID NO 3
<211> LENGTH: 32
<212> TYPE: DNA
<213> ORGANISM: Artificial Sequence
<220> FEATURE:
<223> OTHER INFORMATION: Synthetic Construct

<400> SEQUENCE: 3
tggtctgccg actggacgaa cgagggagcg ta                              32

<210> SEQ ID NO 4
<211> LENGTH: 32
<212> TYPE: DNA
<213> ORGANISM: Artificial Sequence
<220> FEATURE:
<223> OTHER INFORMATION: Synthetic Construct

<400> SEQUENCE: 4
tacgctccct cgttcgtcca gtcggcagac ca                              32

<210> SEQ ID NO 5
<211> LENGTH: 31
<212> TYPE: DNA
<213> ORGANISM: Artificial Sequence
<220> FEATURE:
<223> OTHER INFORMATION: synthetic construct

<400> SEQUENCE: 5
acaggtcgcc gttgaggcta ccagcggaca g                               31

<210> SEQ ID NO 6
<211> LENGTH: 31
<212> TYPE: DNA
<213> ORGANISM: Artificial Sequence
<220> FEATURE:
<223> OTHER INFORMATION: synthetic construct

<400> SEQUENCE: 6
tggtctgccg actggacgaa cgagggagcg t                               31

<210> SEQ ID NO 7
<211> LENGTH: 32
<212> TYPE: DNA
<213> ORGANISM: Artificial Sequence
<220> FEATURE:
<223> OTHER INFORMATION: Synthetic Construct

<400> SEQUENCE: 7
tagagcccag cacgactcgc cgtatcagcg ga                          32

<210> SEQ ID NO 8
<211> LENGTH: 32
<212> TYPE: DNA
<213> ORGANISM: Artificial Sequence
<220> FEATURE:
<223> OTHER INFORMATION: Synthetic Construct

<400> SEQUENCE: 8
tccgctgata cggcgagtcg tgctgggctc ta                          32

<210> SEQ ID NO 9
<211> LENGTH: 32
<212> TYPE: DNA
<213> ORGANISM: Artificial Sequence
<220> FEATURE:
<223> OTHER INFORMATION: Synthetic Construct

<400> SEQUENCE: 9
acgcttcggt cgctacgcac accaacccgt ga                          32

<210> SEQ ID NO 10
<211> LENGTH: 32
<212> TYPE: DNA
<213> ORGANISM: Artificial Sequence
<220> FEATURE:
<223> OTHER INFORMATION: Synthetic Construct

<400> SEQUENCE: 10
tcacgggttg gtgtgcgtag cgaccgaagc gt                          32

<210> SEQ ID NO 11
<211> LENGTH: 31
<212> TYPE: DNA
<213> ORGANISM: Artificial Sequence
<220> FEATURE:
<223> OTHER INFORMATION: synthetic construct

<400> SEQUENCE: 11
tagagcccag cacgactcgc cgtatcagcg g                           31

<210> SEQ ID NO 12
<211> LENGTH: 31
<212> TYPE: DNA
<213> ORGANISM: Artificial Sequence
<220> FEATURE:
<223> OTHER INFORMATION: Synthetic construct

<400> SEQUENCE: 12
acgcttcggt cgctacgcac accaacccgt g                           31

<210> SEQ ID NO 13
<211> LENGTH: 32
<212> TYPE: DNA
<213> ORGANISM: Artificial Sequence
<220> FEATURE:
<223> OTHER INFORMATION: Synthetic construct

<400> SEQUENCE: 13
tggtcttctg acttgacgaa cgagtgagcg ta                          32

```
<210> SEQ ID NO 14
<211> LENGTH: 32
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: n is inosine
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (21)..(21)
<223> OTHER INFORMATION: n is inosine

<400> SEQUENCE: 14
tggtctgnng antggacgaa ngagggagcg ta                                 32

<210> SEQ ID NO 15
<211> LENGTH: 32
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (39)..(39)
<223> OTHER INFORMATION: n is inosine
<220> FEATURE:
<221> NAME/KEY: misc_feature
<222> LOCATION: (52)..(52)
<223> OTHER INFORMATION: n is inosine

<400> SEQUENCE: 15
tggtctgncg actggacgaa ngagggagcg ta                                 32
```